US008396561B2

(12) United States Patent  
Pezaris et al.

(10) Patent No.: US 8,396,561 B2  
(45) Date of Patent: Mar. 12, 2013

(54) VISUAL PROSTHESIS AND METHODS OF CREATING VISUAL PERCEPTIONS

(75) Inventors: John S. Pezaris, Cambridge, MA (US); R. Clay Reid, Cambridge, MA (US); Emad N. Eskandar, Nahant, MA (US)

(73) Assignees: The General Hospital Corporation, Boston, MA (US); President and Fellows of Harvard College, Cambridge, MA (US)

( * ) Notice: Subject to any disclaimer, the term of this patent is extended or adjusted under 35 U.S.C. 154(b) by 580 days.

(21) Appl. No.: 12/520,741

(22) PCT Filed: Dec. 20, 2007

(86) PCT No.: PCT/US2007/026274  
§ 371 (c)(1), (2), (4) Date: Dec. 11, 2009

(87) PCT Pub. No.: WO2008/079388  
PCT Pub. Date: Jul. 3, 2008

(65) Prior Publication Data  
US 2010/0094382 A1     Apr. 15, 2010

Related U.S. Application Data

(60) Provisional application No. 60/876,837, filed on Dec. 22, 2006.

(51) Int. Cl.  
*A61N 1/00* (2006.01)

(52) U.S. Cl. .................................................. 607/54

(58) Field of Classification Search ............ 607/54  
See application file for complete search history.

(56) References Cited

U.S. PATENT DOCUMENTS

| 4,628,933 | A | 12/1986 | Michelson |
|---|---|---|---|
| 2002/0010496 | A1 | 1/2002 | Greenberg et al. |
| 2003/0114886 | A1 | 6/2003 | Gluckman et al. |
| 2003/0151541 | A1 | 8/2003 | Oswald et al. |
| 2004/0030383 | A1 | 2/2004 | Havey et al. |
| 2004/0236389 | A1 | 11/2004 | Fink et al. |
| 2006/0135862 | A1* | 6/2006 | Tootle et al. ............ 600/373 |
| 2009/0220425 | A1* | 9/2009 | Moxon et al. ........... 424/9.2 |
| 2011/0087315 | A1* | 4/2011 | Richardson-Burns et al. ............ 607/116 |

OTHER PUBLICATIONS

Li et al., "Temporal Properties of Retinal Ganglion Cell Responses to Local Transretinal Current Stimuli in the Frog Retina," *Vision Research* 45:263-273, 2005.  
Reid, R. Clay, "Processing of Visual Scenes by the LGN," *Abstract*, NIH Grant No. 1R01REY012815-01, 2000.  
Yagi et al., Biohybrid Retinal Implant: Research and Development Update in 2005: Proceedings of the 2nd *International IEEE EMBS Conference on Neural Engineering*—Arlington, VA, pp. v-viii, Mar. 16-19, 2005.  
International Search Report for PCT/US07/26274 (mailed Jun. 24, 2008).

\* cited by examiner

*Primary Examiner* — George Manuel  
*Assistant Examiner* — Robert N Wieland  
(74) *Attorney, Agent, or Firm* — Clark & Elbing LLP

(57) ABSTRACT

A visual prosthesis and methods of allowing a subject to view visual information from an artificial source are provided. The visual prosthesis has one or more electrodes operative to deliver electrical signals to a lateral geniculate nucleus of a mammal, a power supply operative to provide power to the electrodes, a visual information translator operatively connected to the electrode array, and a visual sensor operatively connected to the visual information translator. The visual prosthesis is operative to translate visual information into an electrical signal and transmit the electrical signal to electrodes to stimulate brain activity to recognize visual information.

20 Claims, 17 Drawing Sheets

A

B

VISUAL PROSTHESIS AND METHODS OF CREATING VISUAL PERCEPTIONS

This application is the U.S. National Stage of International Application PCT/US2007/026274, filed Dec. 20, 2007, which in turn claims benefit of U.S. Provisional Application No. 60/876,837, filed Dec. 22, 2006, each of which is hereby incorporated by reference.

STATEMENT AS TO FEDERALLY FUNDED RESEARCH

The invention was made with support from NIH under grant Nos. R01EY12815 and P30 EY12196. The government has certain rights to the invention.

FIELD OF THE INVENTION

The invention relates to the field of visual prosthetics and methods of allowing a subject to view visual information from an artificial source, e.g., by stimulating the lateral geniculate nucleus.

BACKGROUND OF THE INVENTION

For those unfortunate enough to have lost vision because of accident or diseases such as retinitis pigmentosa, macular degeneration, or glaucoma, restoration of function would mean a tremendous increase in the quality of life.

Existing approaches for replacement of visual function vary widely, e.g., extracranial devices, intra-ocular devices, and intracranial devices.

Extracranial approaches replace the sense of vision by mapping to another sense, such as auditory or tactile, or by electrically stimulating visually-relevant structures. All of these approaches suffer because they only provide a surrogate sensation and do not create visual perception. The shortcomings, which include poor spatial and temporal resolution, cumbersome equipment, and objectionable side-effects, have prevented such approaches from gaining acceptance beyond that of parlor-room curiosity.

Others have tried to restore visual perceptions by stimulating the outer (epi-) or inner (sub-) structures of the retina, by adjusting the geometry of the retina to optimize remaining function, or by directly stimulating the optic nerve. The epi- and sub-retinal approaches place electronic devices at the outer or inner surfaces of the retina, respectively. While initial results from these efforts are interesting, the retina is a delicate structure that does not take well to manipulation, and long-term stability remains a serious concern. Further, for epi-retinal devices in particular, the architecture of the outer retina is not ideal because stimulating the ganglion cells at a given point will unavoidably stimulate axons from retinotopically distant cells, which will make it impossible to create detailed visual percepts. For the subretinal devices under investigation, limitations on the amount of optically-deliverable power preclude operation at all but the highest levels of illumination.

Another approach seeks to deliver electrical stimulation directly to the primary visual cortex and entirely bypasses the early stages of the visual system. However, the complexity of cellular response in the primary visual cortex, and the relative inaccessibility of the important foveal representation prevent the primary visual cortex from being a good target for an implant. Therefore, creation of an effective synthetic visual experience of more than passing detail from an implant in the cortex is quite difficult.

It is an object of the present invention to provide a visual prosthesis and methods of creating visual perceptions in a mammal that reduce or wholly overcome some or all of the difficulties inherent in prior known devices. Particular objects and advantages of the invention will be apparent to those skilled in the art, in view of the following disclosure of the invention and detailed description of certain preferred embodiments. These and other objects are satisfied by the methods and products disclosed herein.

SUMMARY OF THE INVENTION

The lateral geniculate nucleus (LGN) of the thalamus is the part of the thalamus that relays visual information from the eye to the cerebral cortex. We have discovered that delivering electrical stimulation in the LGN can induce spatially accurate visual percepts in awake behaving primates. In these experiments, animals learned to make specific eye movements to discrete areas in response to the stimulation. This technique can be used in humans to potentially enhance or restore vision in cases of macular degeneration, retinitis pigmentosa, or other injuries to the eyes from trauma, cancer, etc., or medically-necessary enucleation. This approach has significant advantages over other approaches for visual prostheses such as stimulation of the retina or occipital cortex.

In accordance with a first aspect, a visual prosthesis has at least one electrode operative to deliver an electrical signal to a lateral geniculate nucleus of a mammal. The prosthesis also has a power supply operative to provide power to the electrode, a visual information translator operatively connected to the electrode, and a visual sensor operatively connected to the visual information translator.

According to certain preferred embodiments, the prosthesis may also include a gaze locator operatively connected to the visual sensor. A gaze locator can be useful for directing the visual sensor to collect visual information coinciding with subject's gaze.

According to other preferred embodiments, the electrodes of the visual prosthesis may be in the form of an array or bundle, wherein each electrode of the array or bundle is operative to deliver electrical signals to a lateral geniculate nucleus of a mammal. Providing electrodes in the form of an array or bundle may be advantageous for providing a dense patterning of stimulation.

In certain preferred embodiments, the visual sensor may be a camera, an artificial retina, a microscope, an infrared sensor, a telescope, a light sensing diode, a CCD device, a photodiode array, or a combination thereof The power source may be selected from one or more of a photodiode array, an inductive coil, capacitive plates, a thermoelectric device, a generator, and a fuel cell. The power source may be rechargeable or replaceable in certain embodiments.

In accordance with a second aspect, methods of allowing subjects to view visual information from an artificial source are provided. The methods include operatively connecting one or more electrodes to a lateral geniculate nucleus of a mammal, providing a source of visual information, translating the visual information into an electrical signal, transmitting the electrical signal to the electrodes, and stimulating the lateral geniculate nucleus with the electrical signal through the electrodes in a manner to stimulate a subject's brain activity to recognize visual information.

According to certain preferred embodiments of the second aspect, the method may further include creating a map of the electrodes connected to the lateral geniculate nucleus. Creating a map of the electrodes connected to the lateral geniculate nucleus can be useful for providing patterning of stimulation of the lateral geniculate nucleus. A map may be created through residual visual function or through anatomical means.

In certain preferred embodiments, the visual information is hyperacute. Providing hyperacute visual information may be advantageous for providing a subject with, for example, night vision, microscopic vision, and/or telescopic vision.

According to certain preferred embodiments as described above, a method of allowing subjects to view visual information from an artificial source may further include reading the position of an eye of the subject to provide gaze information, wherein the gaze information determines the origin of visual information.

Certain preferred embodiments of the method of allowing subjects to view visual information from an artificial source may include penetrating each layer of each lateral geniculate nucleus with at least one electrode.

Substantial advantage is achieved by connecting a visual prosthesis to a lateral geniculate nucleus of a mammal and by stimulating the lateral geniculate nucleus of the mammal. In particular, by providing stimulation to the lateral geniculate nucleus of a mammal, the mammal can recognize visual information. This is highly advantageous for restoring sight or for increasing visual perception in a mammal.

The prosthesis and methods of the invention can be used, for example, for restoration of sight to blind or low-vision individuals. Additionally, supernormal sight (e.g., non-visual sensors, different magnifications, and different sensitivities) can be permitted through augmented sensors. In one embodiment, a standard digital camera or video camera is used as the visual sensor. The output of this is coupled to the LGN to provide restoration of sight. In another embodiment, a device sensitive to infrared, ultraviolet, radio waves, particle radiation, sounds, or other non-visual quantities, could be used as the visual sensor. The sensed parameter would be transformed into a visual signal, the interpretation of which would be up to the individual's training. One embodiment includes optics with adjustable magnification such that the implanted patient may range his gaze not only horizontally and vertically, as normal, but also by zooming in and out.

The transfer of information from external sensors into LGN need not be purely electrical; it can have a biological component as well, through the use of an artificial optic nerve. If desired, information transfer can be done wirelessly to an implanted stimulator partially or wholly within the cranial cavity.

In one preferred embodiment, an auxiliary computational device is required to accept signals from an external visual sensor, either a camera or other artificial retina, or a purely computationally synthetic source, and decode these signals into patterns of activation appropriate to the array of stimulation loci.

In another preferred embodiment, a device is used to read the current position of the eyes to adjust the mapping of the external visual sensor to the stimulation array, to adjust the position and orientation of the sensor, or to provide gaze information to a synthetic scene generator.

In another preferred embodiment, the external visual sensor is designed to take the place of one or both of the eyes, implanted such that the ocular muscles control the sensor orientation. This would obviate the need for the mapping mechanism in the previous embodiment.

For a sufficiently high resolution embodiment, additional information may be placed on top of the visual component of a scene. Such information could be relevant to the implanted patient for navigational purposes, as supplementary perceptual analysis, or for entertainment or educational purposes.

Also contemplated as part of the invention is the placement of electrodes and the patterning of phosphenes, specifically placing a regular or semi-regular array or bundle of electrodes to achieve a non-regular placement of phosphenes. Differing placements of electrodes evoke differently colored phosphenes. Thus, by placing multiple electrodes in different laminae (or just different depths) in the LGN that have the same representation in visual space, once can coordinate stimulation across electrodes to produce percepts with varying colors in a controllable fashion.

The visual scene has uniform resolution, just like a computer monitor or a photograph. That is, the number of pixels per unit area is constant, or very nearly so, from one part to the next. The visual system, however, does not have uniform resolution across visual space, as the density of photosensitive elements is much higher near the center of gaze than in the visual periphery. The part of the brain that processes visual information works very hard to integrate our perceptions as we move our eyes about a scene to give the illusion of uniform high resolution, despite the fact that we have high resolution vision for only the central most few degrees of sight.

A prosthesis device that utilizes a non-uniform distribution of sensing and processing elements would be advantageous. Such a non-uniform distribution can be readily achieved by a uniform, on average, placement of simulating electrodes or their equivalent throughout the LGN. When viewed statically, such a system would appear to have points of visual perception that were closer together at the center of visual space and farther apart at the extremes. When viewed dynamically, the visual system of the brain integrates the transient high-resolution information available for the object at the current center of gaze as the eyes move around the visual scene, producing the impression of uniformly high resolution vision.

Active elements, both electrical and biological, that are used to generate phosphenes can be placed with either uniform or non-uniform density in order to approximate the natural non-uniform variation in resolution or to compensate for it and create a uniform resolution, respectively.

Accordingly, in another aspect, the invention features a prosthesis device with an average uniform density of contact placement, e.g., insertion or surface contact, in two or three dimensions across a target brain area, e.g., LGN, so as to achieve a non-uniform density of visual percepts, weighted toward the center of vision, approximating the natural non-uniform distribution of visual resolution.

In a related aspect, the invention features a prosthesis device with a non-uniform density of contact placement, e.g., insertion or surface contact, in two or three dimensions across a target brain area, e.g., LGN, so as to achieve a uniform density of visual percepts, approximating a non-natural even distribution of visual resolution.

These and additional features and advantages of the invention disclosed here will be further understood from the following detailed disclosure.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Various embodiments of the invention are described below with reference to the accompanying drawings in which:

FIG. 13A depicts an example receptive field (RF) map, measured from the same recording location as data for FIG. 12B, and in register with the fixation point location at the center of the panel. Black pixels correspond to locations where the cells respond to black squares in the mapping stimulus, and gray pixels where there was no response. The extent of mapping is the extent of gray pixels. The response for this site is a one-pixel blue peak down and to the right of the fovea. FIG. 13B is an overlaid RF map and electrical saccades. The RF peak is highlighted (crosshair). Overplotted saccades from FIG. 12B demonstrate correspondence between endpoints and RF location with an error comparable to that for optical targets (FIG. 12A, FIG. 14B, and main text). FIGS. 13C-13F depict additional examples of correspondence between RF map and saccades in response to electrical targets. Similar results were found in all three LGNs studied, spanning all four quadrants of visual space, at eccentricities of 2-26°. FIG. 13G is a summary of RF positions (dots) and saccade cluster centers (diamonds). The slight upward bias is typical of the task. Errors for electrical saccades were comparable to, although somewhat larger than, those for optical saccades (FIG. 14B).

Figure 1:
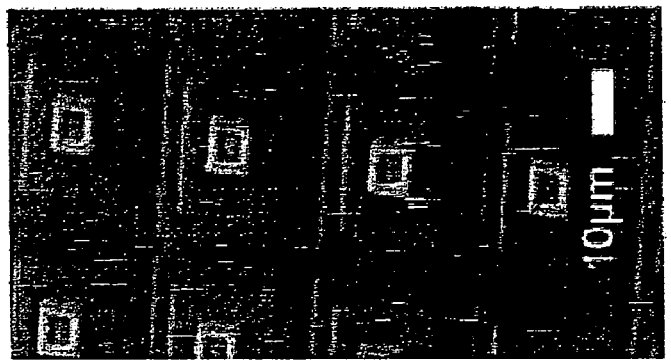
FIG. 1A is depiction of an implantable electrode array, the electrodes of which extend into the layers of the lateral geniculate nucleus.
FIG. 1B is a photograph of an implantable electrode array, the electrodes of which remain on the surface of the lateral geniculate nucleus.
Figure 1:
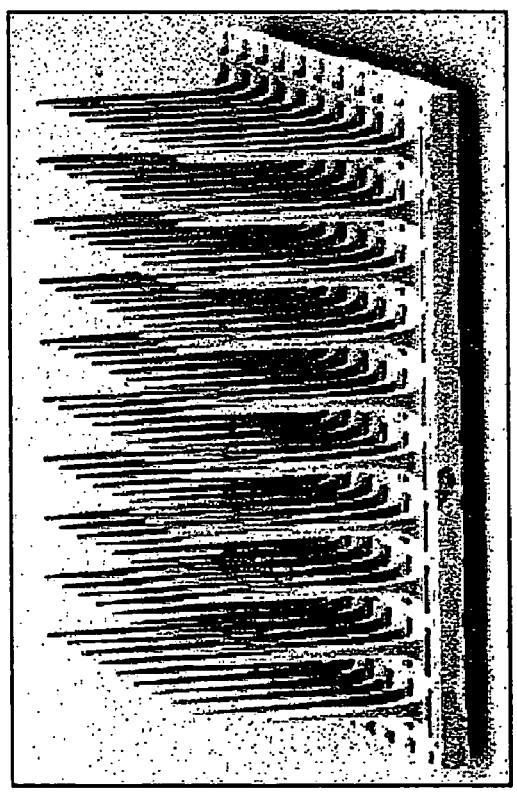

The figures referred to above are not drawn necessarily to scale and should be understood to present a representation of the invention, illustrative of the principles involved. Some features of the visual prosthesis and methods of creating visual perceptions depicted in the drawings have been enlarged or distorted relative to others to facilitate explanation and understanding. The same reference numbers are used in the drawings for similar or identical components and features shown in various alternative embodiments. Visual prosthesis and methods of creating visual perceptions as disclosed herein will have configurations and components determined, in part, by the intended application and environment in which they are used.

DETAILED DESCRIPTION OF THE INVENTION

The examples given here are only illustrative, and it should be understood that these methods are appropriate for any mammal. A person skilled in the art, having the benefit of this disclosure, would know how to adapt the examples given for their particular purpose.

The lateral geniculate nucleus is a part of the thalamus that relays signals from the retina to the primary visual cortex. The lateral geniculate nucleus is an area not normally affected by diseases that attack ocular structures and has a simple structure that may be readily mapped in visual space. The perception of a reasonable facsimile of a visual scene, or visual information, may be created in an otherwise blind or low-vision subject by directly stimulating the lateral geniculate nucleus by, for example, inserting electrodes into the lateral geniculate nucleus.

Each of the two lateral geniculate nuclei of a mammal (one per cranial hemisphere) covers approximately one half of the visual space represented by the two retinae. Whereas positions on the retina directly map to points in visual space through the eye's optics, positions along the surface of the lateral geniculate nucleus directly map to points on the retinal surface through the optic nerves. This mapping allows the assignment of a stimulation locus to a point in perceptual space based on its location along the lateral geniculate nucleus surface. Stimulation by an electrode at a given point in or on the lateral geniculate nucleus produces an event in a well-defined location in perceptual space. In addition, stimulation at differing depths of the lateral geniculate nucleus can produce different types of visual percepts, such as blue versus uncolored, or light versus dark, based on the depth from the surface. This is because the lateral geniculate nucleus is arranged in a laminar structure where different laminae are responsive to different visual features. While some segregation exists in the retina, the microscopic separation between layers and their extreme thinness precludes preferentially stimulating different types of neurons.

The invention provides a method for allowing a subject to view visual information from an artificial source. The method includes operatively connecting one or more electrodes to a lateral geniculate nucleus of a mammal, providing a source of visual information, translating the visual information into an electrical signal, transmitting the electrical signal to the electrodes, and stimulating the lateral geniculate nucleus with the electrical signal through the electrodes in a manner to stimulate brain activity to recognize visual information.

The term subject is intended to include living organisms such as mammals. Examples of subjects include humans, dogs, cats, mice, rats, and primates. The term visual information is intended to include, for example, any information that can be perceived visually, or information relating to a subject's surroundings. Such visual information may include, for example, color, contrast, shape, texture, brightness, text, graphic images, shadow, animation, distance, movement, orientation, depth, and navigation. The term "artificial source" is intended to include any source other than an animal's eye, for example, a camera, another subject, a telescope, a microscope, an artificial retina, a photodiode, a photodiode array, a thought, a visualization, a charged coupled device (CCD), and purely computational synthetic sources.

As the thalamus is a deep-brain structure, lateral geniculate nucleus prosthetics are not exposed to the forces of rapid accelerations as are retinal implants. For thalamic implants that have physical external connections or leads (as opposed to ones with wireless connections) the path length from the thalamus to the external surface of the skull will tend to firmly hold the connections in place, especially for neutral-buoyancy implants. In addition, there are well-developed clinical approaches to deep-brain stimulation and recording, including chronic deep-brain implants routinely used to control Parkinsonian tremor and epilepsy.

The phrase "operatively connecting one or more electrodes to a lateral geniculate nucleus of a mammal" should be understood here to include, for example, placing one or more electrodes in contact with the cells comprising the lateral geniculate nucleus. The term "in contact" should be understood to include, for example, surface-to-surface contact and electrical contact. Other methods of operatively connecting the electrodes and the neurons of the lateral geniculate nucleus will be known to those of skill in the art having the benefit of this disclosure. To operatively connect the electrodes, for example, the electrodes may be surgically implanted into the lateral geniculate nucleus or onto the surface of the lateral geniculate nucleus. In certain preferred embodiments, one or more of the electrodes may be on the surface of the lateral geniculate nucleus and others may extend into or in-between the cells of the lateral geniculate nucleus. For example, FIG. 1A shows an electrode array that will be implanted with the electrodes extending into the neuronal layers of the lateral geniculate nucleus. FIG. 1B shows an electrode array that will be implanted onto the surface of the lateral geniculate nucleus.

In certain preferred embodiments, the source of visual information may include, for example a camera, a telescope, a microscope, an artificial retina, a photodiode, a photodiode array, a charged coupled device (CCD), a visualization, a thought, and/or a purely computational synthetic source. These sources of visual information may be operatively connected to the device that translates the visual signal or information into electronic information. The source of visual information may itself be operative to transform the visual information into electrical information.

For example, exact placement of electrodes into, on, in-between, or within the lateral geniculate nucleus can be used to predetermine the visual percept for each stimulation point with the aide of high-resolution anatomical mapping. Complex patterning to generate stable percepts of visual information may be achieved according to certain preferred embodiments, for example, by delivering bursts of electrical signals versus tonic signals, or by providing electrical signals that sweep across the electrodes or electrode array or bundle.

The term "translating the visual information into an electrical signal" is intended to include, for example, computationally or otherwise transforming the visual information into waveforms having a signal intensity and frequency effective to stimulate the neurons of the lateral geniculate nucleus, and thereby the brain of the subject to interpret or recognize the pattern of electrical stimulation as visual information. For example, a device that translates visual information into electrical signals may include a computer or processor with digital signal processing and a digital to analog converter or other device operative for generating electrical impulses. The computer or processor may be operative, for example, to calculate various transformations of the visual signal, such as spatial Gaussian or Gabor filters and temporal filters such as the difference of alpha functions. For example, a device that translates visual information into electrical signals may include a Gaussian or Gabor filter, an edge detector, a color detector, a foreground/background separator, and/or an object detector.

According to certain preferred embodiments, the visual information translator, i.e., a device that translate visual information into an electrical signal, is operatively connected to the electrode wirelessly. In other embodiments, the visual information translator is operatively connected to the electrode via a lead. Suitable leads include, for example, fine wires, bundled wires, cultured neurons, coated wires, or wires coated in a biocompatible insulating material. In another preferred embodiment, the delivery of visual information to the lateral geniculate nucleus may be through an optic-nerve-like structure of neurons cultured to project into the lateral geniculate nucleus and synapse upon cells therein. Such an artificial optic nerve would be preferentially interfaced with electronic or biological source of visual information to provide the visual information that will be converted into electrical signals. In certain preferred embodiments, the visual information translator includes, or is coupled to, a stimulator. The stimulator may be operative to receive a signal from, or as part of, the visual information translator and to transmit an electrical signal to the electrode or electrodes.

According to certain preferred embodiments, a visual sensor may be operatively connected to the visual information translator. For example, a visual sensor or source of visual information may contain a microprocessor or digital signal processor operative to translate the visual information into electrical signals, a visual sensor may also be connected via leads or wirelessly to the visual information translator.

The term electrical signal, as understood here, may include, for example, electrical impulses and signals with varying degrees of voltage, current, frequency, pulse duration, and wavelength. The waveform and frequency of the electrical signal may be varied to provide effective stimulation of visually evoked potentials with the least destructive impact on the lateral geniculate nucleus. In certain preferred embodiments, the electrical signal should take into account the following physiological factors: (1) the threshold for exciting lateral geniculate nucleus neurons in terms of voltage, current, and optimal waveform, (2) the minimum stimulus time required to produce a visual pixel, (3) the dynamic range of the stimulated neuron, (4) the amount of movement of the exciting electrical field that the visual system can detect, (5) electrode impedance, and (6) the minimum size of the stimulating electrical field. In other preferred embodiments the electrical signal may include, for example, (a) not more than about 0.1 to 10 Volts and/or about 0.1 to 100 milliamps; (b) a biphasic (+/−) waveform (avoiding direct-coupled monophasic waveforms); (c) a pulse duration of about 0.1 to about 10 milliseconds per phase; and (d) a frequency of about 10 to about 500 Hertz. Preferable signals are biphasic pulses of about 1 millisecond duration of about 5 Volts delivered at about 100 Hertz. In other certain preferred embodiments, the stimulation with electrical signals may include patterned impulses. For example, patterned stimulation would have similar ranges of current and voltage, but would be delivered in an aperiodic manner. For example, the instantaneous frequency would change potentially from pulse to pulse. The instantaneous frequency (or time between successive pulses) can range from about 10 Hz to about 1000 Hz or from about 1 to about 100 ms. In accordance with certain preferred embodiments, the stimulation may be coordinated between the electrodes of an array or bundle.

In certain preferred embodiments, the electrical signals include repetitive pulse waveforms such as, but not limited to, square waves, sinusoidal pulses, triangle waves, and/or square pulses. In other preferred embodiments, the electrical signals include square waves, sinusoidal pulses, triangle waves, sync pulses, and/or square pulses; the electrical signals have a signal strength that varies from about 0.01 Volt to about 10 Volts, and/or about 0.01 mA to about 100 mA; and the electrical signals have a frequency that varies from about 1 Hz to about 500 Hz.

The electrical signal provided to the electrode or electrodes is, according to certain preferred embodiments, one sufficient to depolarize the neurons of the lateral geniculate nucleus and evoke an action potential therefrom, which will propagate the signal. The electrical signal may also preferably produce an electric current or voltage field capable of spreading in the lateral geniculate nucleus to a region approximately 10-50 micrometers in diameter.

Transmitting the electrical signal to the electrodes, in accordance with certain preferred embodiments, may be done wirelessly, with wire leads, with cultured neuronal leads, with natural neuronal leads, or in any fashion determined to be appropriate for a particular purpose by one of skill in the art having the benefit of this disclosure. For example, the electrical signal may be transmitted by a wireless signal transmitter, such as the BION system developed at the Illinois Institute of Technology (Troyk, Brown, Moore, Loeb, "Development of BION technology for functional electrical stimulation: bidirectional telemetry", Proc. IEEE-EMBS, 2001). According to certain preferred embodiments, the electrical signals are transmitted wirelessly to the electrodes by, for example, a wireless transmitter, inductive coupling coils, capacitive coupling plates, or infrared transmitter. According to other preferred embodiments, electrical signals are transmitted via biological leads to the brain, for example, by cultured neurons or nerve bundles synapsing on the lateral geniculate nucleus. In certain other preferred embodiments, the electrical signals are transmitted via wire leads to the electrodes, for example, by stainless steel, copper, tungsten, titanium, platinum/iridium, or other insulated metallic wires, carbon, boron, or silicon or other conductive fibers, protected from the body with biocompatible materials such as parylene, formvar, silicone, and/or native oxide. According to certain preferred embodiments, the visual information translator may include an integrated circuit or other device that can translate visual signals into electrical signals. The integrated circuit may include, for example, electronic devices for amplifying, shaping, triggering, and timing the inputs from the visual sensors to form electrical signals that are optimal neural excitation signals. For example, signals that are able to stimulate brain activity to recognize visual information. The translated visual signals may be transmitted to one or more electrodes in the array or bundle as appropriate; for example, the visual signals that are translated into electrical signals will be delivered or transmitted to the electrode or electrodes which correspond to the mapped place in visual space. For example, the electrical signal can be patterned or the like to create a visual scene.

The human neural transmission channel has an upper frequency bandwidth limit between 1 Hz and 2 kHz. It is desirable to limit the frequency of the electrical signal to within this bandwidth, and perhaps to a small portion of this bandwidth. In certain preferred embodiments, the frequency of the electrical signal will be between about 5 Hz and about 500 Hz.

According to certain preferred embodiments, the lateral geniculate nucleus may be stimulated in a way to elicit the brain of the subject to interpret, recognize, or integrate the electrical signal as visual information. That is, the lateral geniculate nucleus may be stimulated with the electrical signal through the implanted electrodes in a manner that stimulates brain activity to recognize visual information. The brain may recognize the information, for example, as patterned phosphenes, as still images, as moving images, as outlines of images, as schematic representations of images, as shadow and light images, as color images, as colorless or reduced-color images, and/or as gray scale images.

The lateral geniculate nucleus may be stimulated with a sufficiently dense number of electrodes or a sufficiently dense stimulation array or bundle. Such a sufficiently dense number of electrodes may, for example, completely cover the perceptual space of the subject, may cover only part of the visual space. In one preferred embodiment, a collection of fine stimulating electrodes terminates in the lateral geniculate nucleus; the origins of the electrodes connect to circuitry via leads for the receipt of visual signals to create neural activity in the lateral geniculate nucleus through stimulation with electrical signals. The locus of cells nearby a given electrode tip or site of termination may be activated, for example, by the application of appropriate levels of current between the electrode and a remote reference, or between neighboring electrodes, or between an electrode and an encompassing shield. The excitation of small loci of cells may deliver specific activity to the lateral geniculate nucleus and generate the perception of luminance (lightness or darkness, with or without associated color aspect, depending on simulating parameters and electrode position within the lateral geniculate nucleus) at that location in visual space. The aggregate stimulation of an electrode array or bundle may combine into a visual scene made of visual information that may be limited in resolution by the number, spacing, and placement of the electrodes.

According to certain preferred embodiments, the electrical signals may be transmitted to the electrodes in a pattern. The pattern may correspond, for example, to the visual information, such that the electrode corresponding to an object in the subject's visual space will be transmitted to the corresponding group of neurons in the lateral geniculate nucleus. A two-dimensional electrode array or bundle, according to certain preferred embodiments, may take the form of numerous different patterns by staggering the electrodes, offsetting alternate rows, randomly eliminating selected electrodes in various rows or columns, etc. The electrodes of the prosthesis of certain embodiments may include an array of short, rod-like conductors extending from a lower surface of the prosthesis. The electrodes are disposed in a regular array to form a "bed of nails" configuration which contacts the lateral geniculate nucleus neurons, for example see FIG. 1A. In other preferred embodiments, an electrode array or bundle may only contact the surface of the lateral geniculate nucleus; such an array is shown in FIG. 1B. FIG. 1A is an electrode array from Dick Normann's laboratory (University of Utah) and is provided as an exemplary array for use in this invention. Other types of electrodes are also appropriate for use in this invention, and one with skill in the art, having the benefit of this disclosure, would be able to determine the appropriate electrode array for a particular purpose. In one example, electrodes resembling Ad-Tech 8-contact micro-wire bundles are used in the methods and prostheses of the invention (see, for example, part number WB08R-SP00x-000 from Ad-Tech).

According to certain preferred embodiments, each layer of the lateral geniculate nucleus will contain at least one terminus of an electrode of the prosthesis terminating therein. That is, at least one electrode of the prosthesis will terminate in each layer of the lateral geniculate nucleus. Preferably, multiple electrodes will terminate in each layer to provide a dense stimulation array. According to certain other preferred embodiments, the method of allowing an individual to view visual information from an artificial source further provides penetrating each lateral geniculate nucleus with at least one electrode. That is, each of the two lateral geniculate nuclei will have at least one electrode terminating in and operatively connected to it for stimulation with electrical signals. Certain preferred embodiments of the method also include penetrating each layer of each lateral geniculate nucleus with at least one electrode. As understood here, penetrating each layer of each lateral geniculate nucleus with at least one electrode should be understood to include at least one electrode terminating in each of the layers of each lateral geniculate nucleus. Preferably, multiple electrodes will terminate in each layer to provide a dense stimulation array.

The phrase "creating a map of the electrode connected to the lateral geniculate nucleus" is intended to include making a chart or diagram of where in visual space each electrode stimulates the lateral geniculate nucleus. For example, a map may be created because positions on the retina directly map to points in visual space through the eye's optics, positions within the lateral geniculate nucleus directly map to points on the retinal surface through the optic nerves. This mapping allows the assignment of a stimulation locus to a point in perceptual space based on its location within the lateral geniculate nucleus. Stimulation by an electrode at a given point on the lateral geniculate nucleus produces an event in a well-defined location in perceptual space. In addition, stimulation at differing depths of the lateral geniculate nucleus produces a sensation of either brightness or darkness with or without any color aspect based on the depth from the surface. This is because the lateral geniculate nucleus is arranged in a laminar structure where different laminae are responsive to different local features (for instance colored versus uncolored, light versus dark). While similar segregation exists in the retina, the microscopic separation between layers and their extreme thinness precludes preferentially stimulating different types of neurons. Mapping techniques are known in the art, such as R. C. Reid, J. Victor and R. Shapley, "The use of m-sequences in the analysis of visual neurons," Visual Neuroscience, 14, 1015-1027 (1997), R. C. Reid, J. D. Victor and R. M. Shapley (1997) "Pseudorandom white noise analysis of the cat visual system: linear receptive field properties," Visual Neuroscience, 14:1015-1027, and R. C. Reid and R. M. Shapley (1992) "The spatial structure of L, M, and Scone inputs to receptive fields in primate lateral geniculate nucleus," Nature, 356:716-718. Other techniques used herein are also well known in the art, including the surgical procedures for implanting Warren D J, Fernandez E, Normann R A "High-resolution two-dimensional spatial mapping of cat striate cortex using a 100-microelectrode array" Neuroscience, (2001) 105(1):19-31; Dobelle W H, Quest D O, Antunes J L, Roberts T S, Girvin J P, "Artificial vision for the blind by electrical stimulation of the visual cortex," Neurosurgery, (1979) 5(4): 521-7; and Yelnik J, Damier P, Demeret S, Gervais D, Bardinet E, Bejjani B P, Francois C, Houeto J L, Arnule I, Dormont D, Galanaud D, Pidoux B, Cornu P, Agid Y., "Localization of stimulating electrodes in patients with Parkinson disease by using a three-dimensional atlas-magnetic resonance imaging coregistration method," J Neurosurg, (2003) 99(1):89-99.

In one preferred embodiment, an auxiliary computational device accepts signals from a source of visual information, i.e., the visual sensor, and decodes these signals into appropriate patterns of activation for the electrodes. In another preferred embodiment, a device is used to read the current position of the eyes to adjust the mapping of the source of visual information to the electrodes, to adjust the position and orientation of the sensor, or to provide gaze information to a synthetic scene generator. For example, if a subject changes their gaze 45° to the left, the gaze information would shift 45° to the left. According to certain preferred embodiments, reading the position of an eye of the mammal to provide gaze information, wherein the gaze information determines the origin of visual information is for example done by providing a gaze locator to track the user's line of sight, for example to communicate information regarding the user's line of sight to the visual sensor and/or to the visual information translator. In certain preferred embodiments, a gaze locator is operatively connected to the visual sensor.

In another preferred embodiment, the source of visual information/the visual sensor is designed to take the place of one or both of the eyes. A source of visual information may be implanted such that the ocular muscles control the source orientation. The terms source of visual information and the visual information sensor are used interchangeably. In certain preferred embodiments, a source of visual information may be, for example be one or more photodetectors mounted in the eye of the subject, or one or more photodetectors or photosensitive circuitry mounted outside of the eye.

In certain preferred embodiments, the prosthesis has a stimulator. The stimulator receives information from the visual information translator and drives the electrodes. The stimulator may be circuitry on an electrode array, it may be circuitry associated with the one or more electrodes, it may be connected via a lead to the electrodes or the electrode array, it may be integral with the visual information translator, it could be connected wirelessly to the electrodes. Examples include isolating stimulators, physiological stimulators, and microstimulators. An example of a stimulator that may be used is the A-M Systems, Inc., Model 2200. A person with skill in the art, having the benefit of this disclosure would be able to choose the correct stimulator for a particular purpose. According to certain preferred embodiments, a stimulator is operatively connected to receive a signal from the visual information translator and to transmit an electrical signal to the electrodes.

In a preferred embodiment, the source of visual information may be a mechanism with greater range or acuity than the normal human eye. This would allow, for example, a subject to see in the dark through an infrared-sensitive device, at microscopic detail through a magnifying device, at great distance through a telescopic device, or even in a modality unrelated to the visual or near-visual electromagnetic spectrum. Once a bio-electric interface has been created to the lateral geniculate nucleus, for example, by implanting of electrodes, any external source whose output can be meaningfully translated to visual space may become a source of visual information. One of these preferred embodiments includes optics with adjustable magnification such that the subject may range his gaze not only horizontally and vertically, but also by zooming in and out. In addition, other additional information may be placed on top of the visual component of a scene. For example, such information could be relevant to the subject for navigational purposes, as supplementary perceptual analysis, or for entertainment or educational purposes. For example, a map of the area a subject is in may be overlaid on top of the other visual information the subject is receiving from other sources. In certain preferred embodiments, the subject's hyperacuity may be greater than normal acuity; for example, the acuity may be greater in spatial, temporal, or spectral terms.

The phrase "transmitting electrical power to the electrodes" is intended to include all methods of transmitting electrical power and power supplies operative to provide power to the electrodes, for example, via wires or wirelessly. The electronic circuitry of the electrodes and other portions of the device require electrical power for operation, and direct connection to a power source is not readily available within the lateral geniculate nucleus. In certain preferred embodiments, power is provided to the electrodes through electromagnetic or radio frequency induction. For example, an inductor coil may be wound or may be formed by photolithographic circuit techniques on a surface of an electrode array housing. In other embodiments, power may be provided, for example, from a photodiode array, a thermoelectric device, a battery, a generator, or a fuel cell. In certain preferred embodiments, the power source is rechargeable or replaceable.

As understood here the term electrode is to be understood to include, for example, fine wires, conductive fibers, neurons, glial cells, Schwann cells, and any other material one of skill in the art would find appropriate for a particular purpose having the benefit of this disclosure. In certain preferred embodiments, the electrodes are of differing length, for example, some electrodes will penetrate further into the neuronal layers of the lateral geniculate nucleus. According to certain preferred embodiments, the electrode conductive material will be a conductive fiber such as carbon, boron or silicon, or a metallic wire such as stainless steel, copper, aluminum, tungsten, titanium, platinum, platinum/iridium or similar alloy, singly or multiply insulated with an outer coating of a biocompatible insulating surface such as silicone, parylene, Teflon, formvar, or native oxide.

Figure 2:
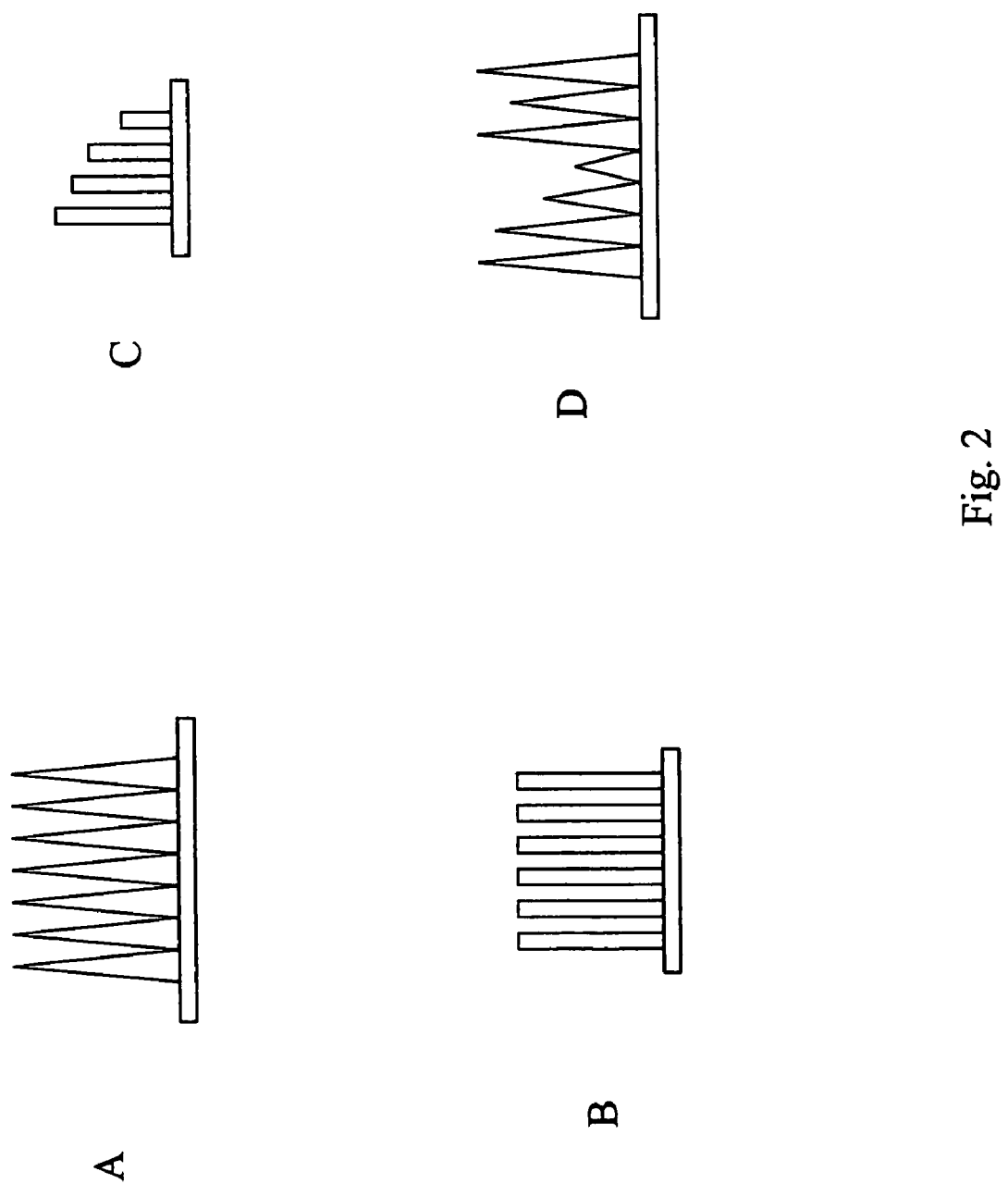
FIG. 2A is a schematic depiction of an electrode array with tapered electrodes.
FIG. 2B is a schematic depiction of an electrode array with untapered electrodes.
FIG. 2C is a schematic depiction of an electrode array with differing length untapered electrodes.
FIG. 2D is a schematic depiction of an electrode array with tapered differing length electrodes.

According to certain preferred embodiments, the shaft of the electrode is tapered, the electrode is from about 0.1 µm to about 100 µm in diameter, the electrodes are of varying lengths, or, in an array of electrodes, wherein each electrode of the array is operative to deliver electrical signal to a lateral geniculate nucleus of a mammal, the electrodes are spaced about 0.1 to 100 µm apart. Electrodes may range in length from about 0.001 µm to about 200 mm. In certain preferred embodiments, the electrodes are biological. Biological electrodes are intended to include electrodes made of cells; for example, the optic nerve could be used as an electrode, neurons could be cultured and directed to synapse onto the lateral geniculate nucleus, or electrically controlled neurons could synapse onto the lateral geniculate nucleus. Examples of different types of electrode arrays can be seen in FIG. 2. FIG. 2A show tapered electrodes, FIG. 2B shows untapered electrodes, FIG. 2C shows untapered electrodes having differing length, and FIG. 2D shows tapered electrodes having differing length.

The term "lead," as used herein, is intended to include, for example, a device that connects devices electrically, biologically, or wirelessly. In certain preferred embodiments, a lead is a wire. In other certain preferred embodiments, the lead is biological, for example, a biological lead may be formed from cultured neurons or naturally existing neuronal pathways such as the optic nerve.

According to certain preferred embodiments, a distance sensor is operatively connected to the visual information translator. Examples of distance sensors include ultrasonic and microwave distance sensors. An ultrasonic distance sensor includes for example an ultrasonic transmitter and receiver and associated circuitry for range finding, such as the Ultrasonic Distance Sensor manufactured by Robotica, Ltd (UK), the Ultra-30 manufactured by Sensix Corporation (US), or the Ultrasonic Sensor by Mitsubishi Electric Automotive America, Inc. (US). The visual information translator in certain preferred embodiments will be operative to translate the signal from a distance sensor into electrical information. The electrical information will be transmitted to the electrodes operatively connected to the lateral geniculate nucleus. The lateral geniculate nucleus will be operative to process the electrical signal such that the subject will be able to tell how far away a certain object is from the subject.

In certain preferred embodiments, an amplifier may be operatively connected to the visual sensor to amplify, shape, and time-process the visual signals. For example, the stimulating signal may be a charge-balanced AC waveform, with no net charge remaining to cause electrolysis and liberate toxic compounds. Also, the signal may be provided to the neurons at a frequency which closely matches the firing rate of the neurons during activation. In certain preferred embodiments, other devices such as capacitors and resistors may be connected to the amplifiers using known techniques to tune the responses thereof to the frequency response bandwidth of the retinal neurons, to shape the output waveform in a charge-balanced square wave format, and to trim the voltage and current outputs to acceptable levels for the neurons.

Figure 3:
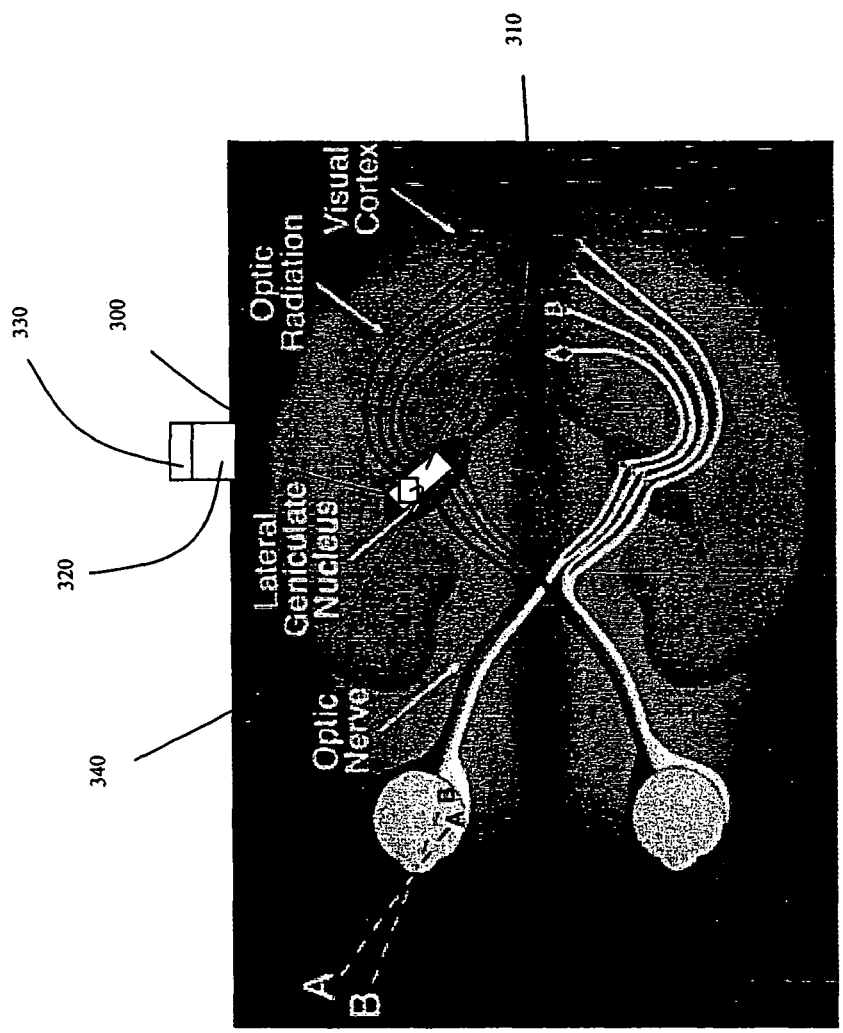
FIG. 3 is a cross-section of a brain with an implanted electrode array.

With reference to FIG. 3, a cross-section of a brain shows the relevant structures, such as the eyes, the optic nerves, and the lateral geniculate nuclei. An electrode array 310 is implanted into a lateral geniculate nucleus. A lead 300 extends from the electrode array to the exterior of the skull. The lead 300 connects the electrode array 310 to the visual information translator 320, and the source of visual information (visual sensor) 330. The power supply 340 is operatively connected to the electrode array to deliver power to the electrodes.

Figure 4:
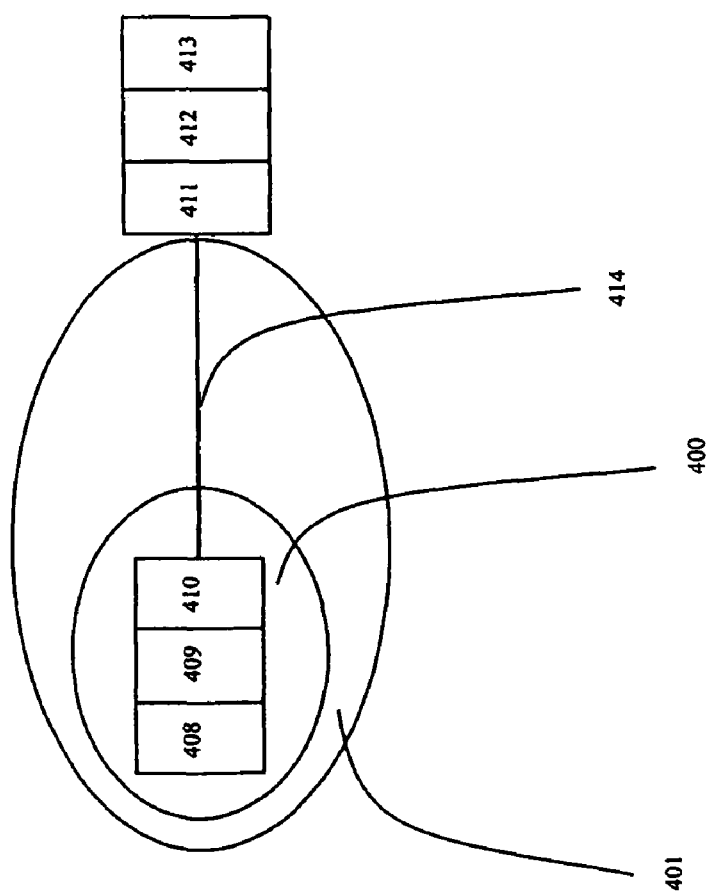
FIG. 4 is a schematic representation of a visual prosthesis.

With reference to FIG. 4, an electrode array 408 is implanted into the lateral geniculate nucleus 400 of the brain 401. The electrode array has a battery 409 and a visual information translator 410 operatively connected to and implanted with the electrode array 408 into the lateral geniculate nucleus 400. The visual information translator 410 is connected via lead 414 to the visual sensor 411. The visual sensor is operatively connected to a gaze locator 412 and an ultrasonic distance sensor 413. The gaze locator 412 and the ultrasonic distance sensor 413 are also operatively connected to the visual information translator through lead 414.

Figure 8:
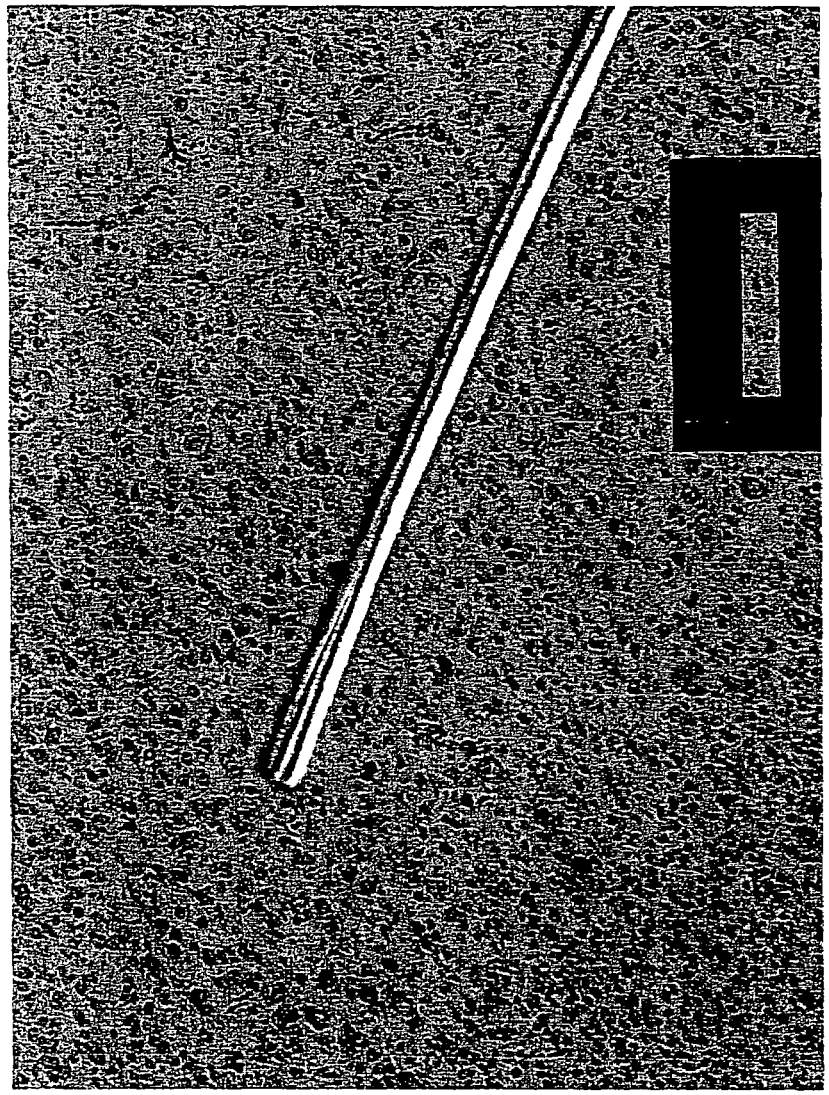
FIG. 8 is a photograph of an electrode implanted into the brain.

In reference to FIG. 8, a photograph shows brain tissue with a group of electrodes, with two of four wires visible, penetrating into the tissue of the brain. The scale bar is 100 micrometers. This photograph demonstrates that such electrodes are implantable into brain tissue and are capable of stimulating the neurons in close physical proximity and in direct contact with the electrodes.

Figure 9:
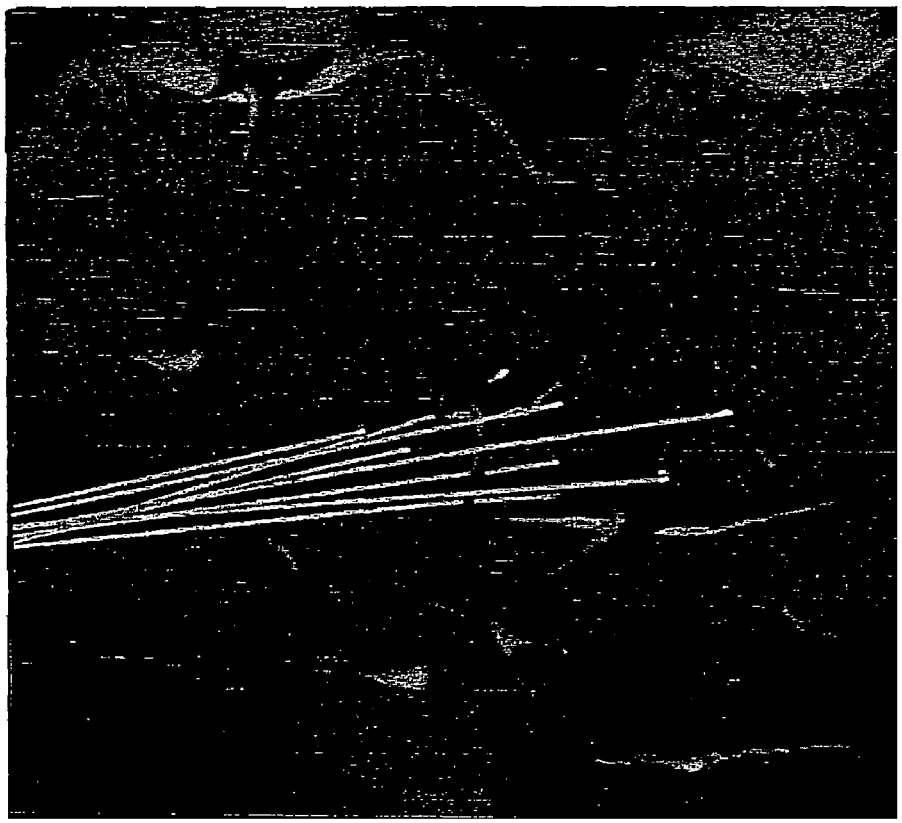
FIG. 9 is a drawing that depicts electrodes implanted into the lateral geniculate nucleus.

FIG. 9 depicts electrodes implanted into the lateral geniculate nucleus. The electrodes are the strands that are placed among the neurons of the lateral geniculate nucleus. The neurons are depicted in with axons and dendrites extending therefrom. Some of the electrodes are depicted in physical contact with the neurons and can directly stimulate those neurons. Other electrodes are placed in close physical proximity to the neurons and are also able to stimulate the neurons.

Figure 10:
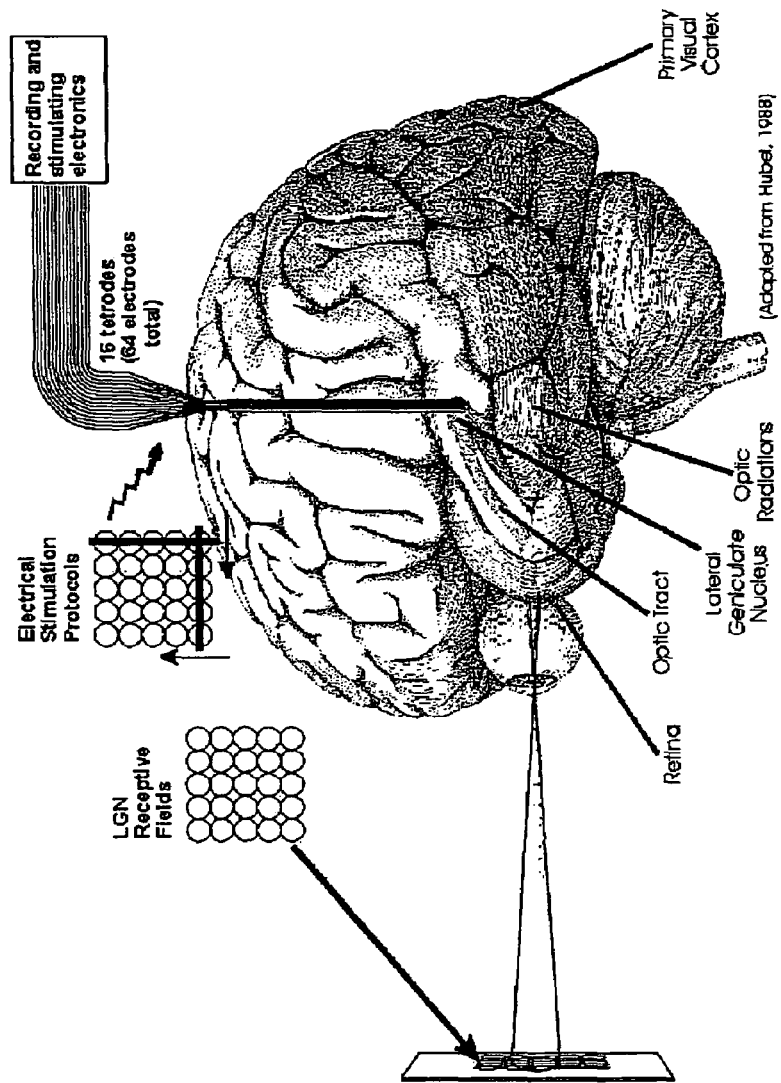
FIG. 10 is a depiction of the Hubel diagram, demonstrating positioning electrodes into the deep brain and stimulating the brain with the electrodes.

In reference to FIG. 10, the Hubel diagram is shown and is taken from Hubel, D. H. (1988) "Eye, Brain, and Vision," New York: W.H. Freeman and Company. The Hubel diagram demonstrates positioning electrodes into the deep brain and stimulating the brain with the electrodes.

EXAMPLE 1

To determine what a monkey sees when electrical stimulation is applied to the LGN, we took advantage of the natural primate reaction to look at any suddenly illuminated point of light. This was used to train monkeys to perform quick, direct eye movements, known as saccades, from one visual target to another. Our findings support the idea that focal electrical stimulation in the LGN creates point-like visual percepts, or phosphenes, that are interpreted as normal visual events.

Fine wire electrodes were placed in the lateral geniculate nucleus of awake behaving monkeys using traditional means. Cells at the end of the electrodes were characterized in visual space, creating a receptive field map, which showed the visual location for which those cells were responsible. Electrical signals were then applied to the wires, stimulating these same neurons, and creating a focal visual percept. We verified that the generated percept corresponded to the receptive field focus by training the animal to look at any spot of light that appeared after having looked at a spot which was straight ahead. In the parlance of the field, the animal was trained to perform visually-guided saccades (normal, rapid eye movements) outward from a central fixation point. We optically presented a series of eight targets on a computer screen, and interleaved this with stimulation through the placed electrode, or with no target at all. An example plot of eye movements measured under these conditions is shown in FIG. 5.

Figure 5:
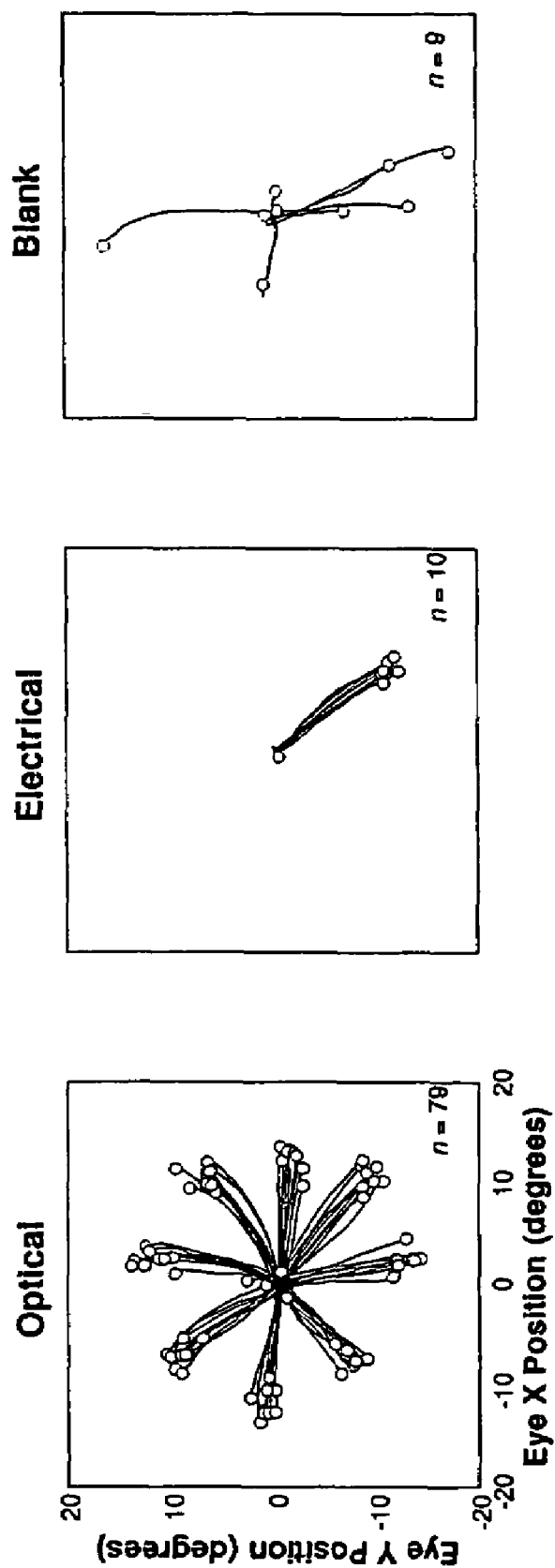
FIG. 5 is graphical representations of eye position traces for optical, electrical, and blank targets.

Referring now to FIG. 5, eye position traces for optical, electrical, and blank targets are shown. Each graph is the overlaying of multiple instances where the animal has started with its eyes pointing in the center of the graph, and makes a gaze change towards a briefly flashed target. The black lines trace out the saccadic eye motion, and the unfilled circles denote the saccade endpoints. In the left plot, the position of the eight optical targets can clearly be elucidated. In the middle plot, the virtual position of the electrically-generated perception can be deduced. To insure the animal was not guessing, the right hand plot shows its behavior when no stimulus is presented. Since the right hand plot shows no consistent behavior, while the middle plot shows behavior analogous to any one of the targets from the left plot, we conclude that the electrically-generated percept is focal and well-defined in space, akin to the normal, optically presented stimuli.

Figure 6:
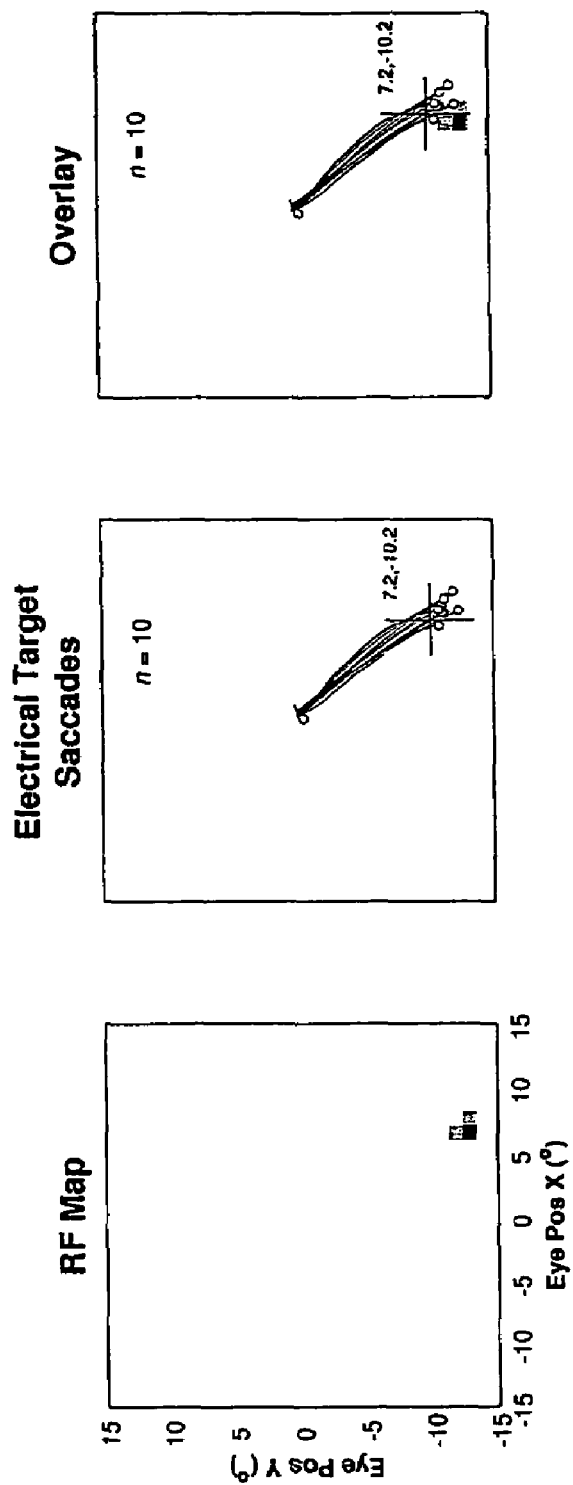
FIG. 6 is graphical representations of predicted and actual target position correspondence.

To verify the correspondence of the measured receptive field map with the visual location of the electrically generated target, in FIG. 6 we show each alone, and then the two overlaid in register. It is possible to perform this check of correspondence because of care taken with calibrating the relationship between screen and eye position.

In reference to FIG. 6, predicted and actual target position correspondence is shown. The left graph shows a sensitivity map for the recording site. Each square represents the activity measured for the corresponding part of visual space. In this example, the cells under study respond best to a location in visual space which is down and to the right. The middle panel is a reproduction of the middle panel from above showing saccades to electrically generated targets. The right panel shows the overlay of these two. This is the kind of graph used in FIG. 7.

To show that this effect is not limited to one particular site, we repeated the experiment multiple times. The next figure shows the correspondence between the RF map (which will be the predicted location of elicited electrical percepts) and the saccade targets. In all three cases, the correspondence is as good as our measurement accuracy.

Figure 7:
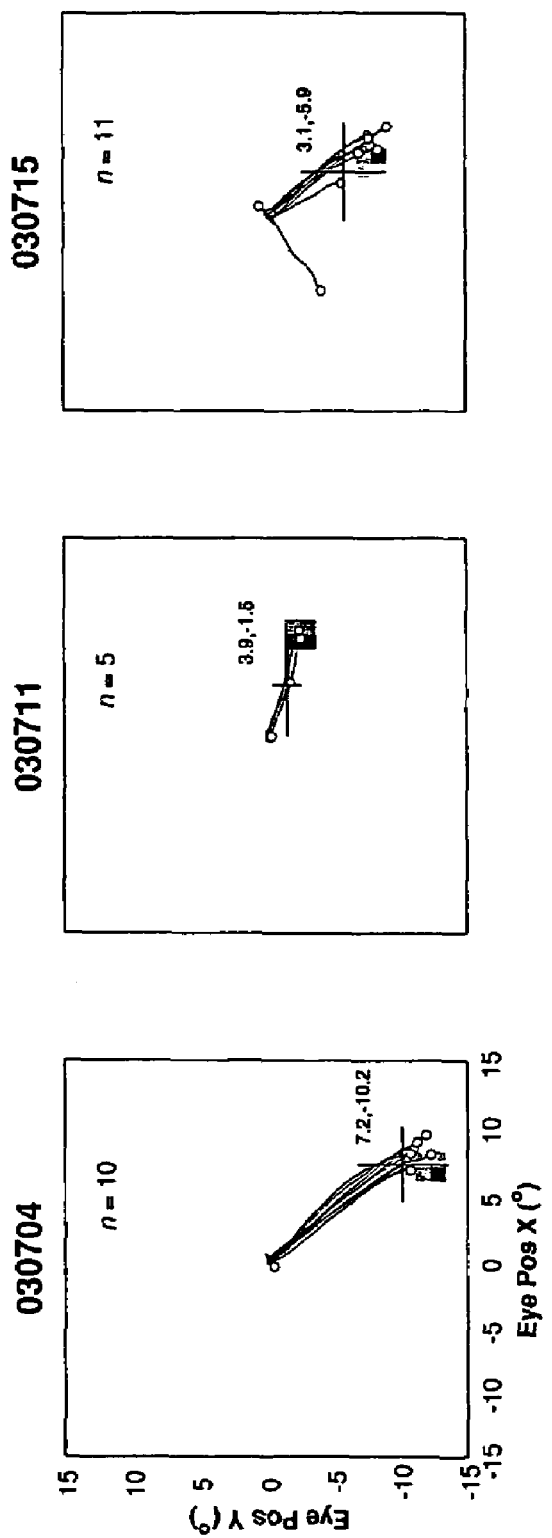
FIG. 7 is a graphical representation of predicted and actual target correspondence for three different stimulus locations.

In reference to FIG. 7, graphs for three example experiments are presented. In each case, when the animal made a saccade, it looked at a point in space, which corresponded to the peak of the receptive field (within experimental uncertainty on the registration of the map and saccades) or did nothing (endpoint circles at the center), with one exception in the rightmost graph where the animal looked elsewhere.

EXAMPLE 2

Figure 11:
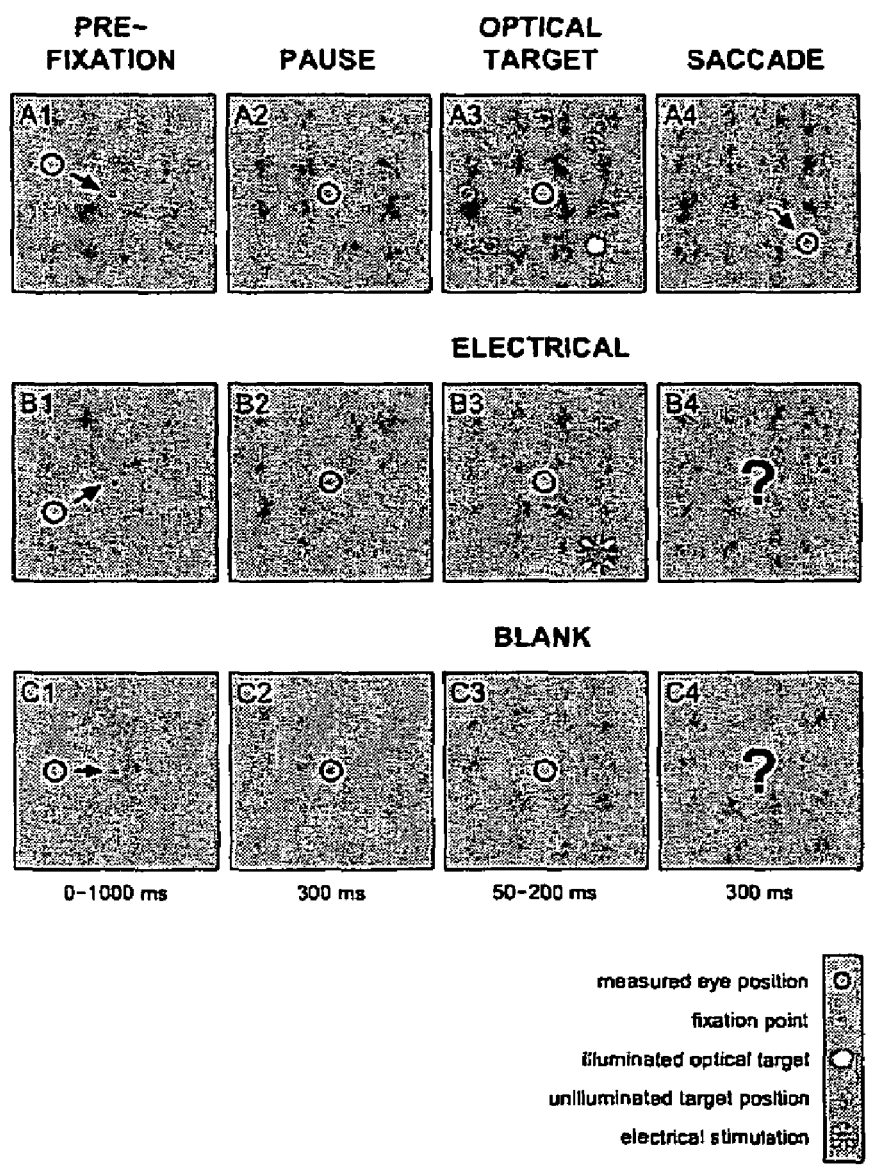
FIG. 11 is a schematic illustration demonstrating the experimental task discussed in Example 2. Columns 1-4 depict schematics of the main behavioral task. Each row represents one of the three conditions, optical, electrical, and blank. Optical trials were rewarded upon successful completion of the task; electrical and blank trials were rewarded on a random schedule with the same average rate as the optical percent correct. (A1-A4) Optical task: primary control. When presented with a fixation point (dot) on a 50 percent gray background, the animal was required to shift gaze position (dark open circle) so as to foveate it. After a brief delay, a target point (filled white circle) was flashed in one of eight possible locations, and the animal required to saccade to the target location; unused targets (open white circles) are indicated on the diagram, but did not appear on the screen. (B1-B4) Electrical task: experimental manipulation. As in A, but target generated through electrical stimulation. (C1-C4) Blank task: secondary control (as in A, but no target was presented).
Figure 12:
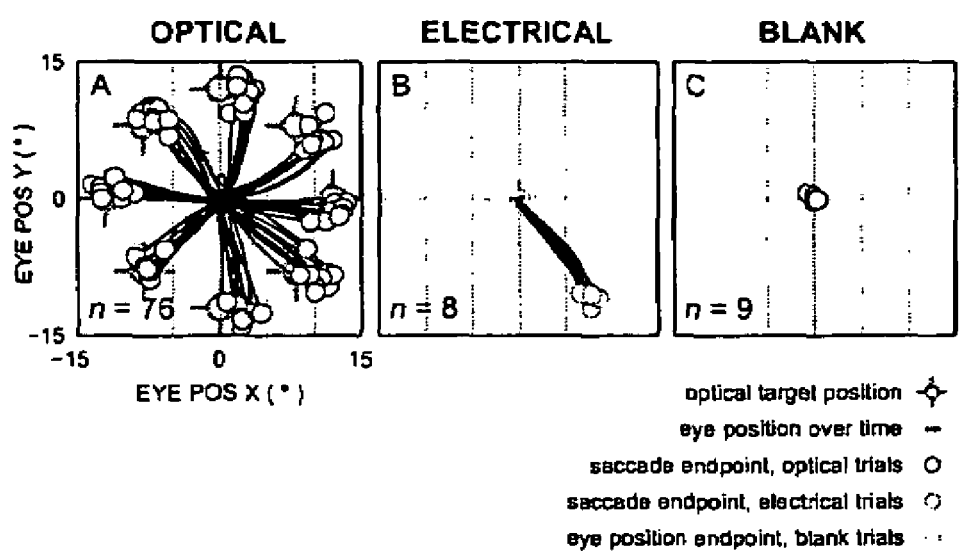
FIG. 12 is a schematic illustration of an example result showing electrical targets are like optical targets. These example results are from a block of trials in the three conditions, optical, electrical, and blank (see FIG. 11). Eye positions (black traces) for the saccade period, corresponding to Column 4 of FIG. 11, start at the center of each panel. Multiple trials are overlaid. (A) Optical condition. Saccade endpoints (circles) cluster around target positions (crosshairs). Offsets between saccade endpoints and target positions are typical of this task and were seen in both animals. (B) Electrical condition. Saccade endpoints (circles) cluster at a position distinct from any of the optical targets. (C) Blank condition. Final gaze position measured at the end of the time window (circles) shows no eye motions were elicited before the 300 ms saccade period ends.

In the series of experiments described in FIG. 2, we first placed a micro-wire bundle electrode, or tetrode, in LGN and mapped the visual responses, or receptive fields, of cells for a given location of the electrode. We then used a center-out saccade task where the animal was required to sit in front of a computer screen and was rewarded for making saccadic eye movements from a central fixation point of light to a target point a short distance away. Optical trials were interleaved with less frequent electrical-stimulation trials (and unstimulated trials, or blanks) to bias the animal towards treating electrical percepts in the same manner as the screen targets (FIG. 11). A set of 100-200 trials were presented in balanced pseudo-random order with respect to optical target position, electrical stimulation, and blank targets (10 conditions in all), for a given experiment. A total of 56 such experiments, each with different electrode placement, were performed in three LGNs of two adult monkeys. Once animals performed consistently above 80% correct while training on optical targets alone, recordings commenced with all three types of trials: optical, electrical, and blank. Both animals immediately generalized to electrical targets in the task, treating electrical targets no differently from optical targets (FIG. 12). In the electrical condition, despite there being no cue on the computer screen, both animals made saccades to a consistent location in space which corresponded to the measured RF characteristics of that experiment's stimulation site. In the blank condition, one animal had a tendency to make a saccade after fixation offset, but to no consistent location; the other animal tended to continue holding its eye position still after fixation offset. Since rewards on electrical and blank trials were given randomly at the same rate as correct optical trials (typically more than 95%), it would not have been possible for the animal to learn the RF location for electrical trials or any specific behavior for blank trials. Each day's electrode placement was different, precise RF locations were not cued, and no searching behavior was seen at the start of the first block of trials. Further, saccades were either not observed in the allotted time window during blank trials (as in FIG. 12C), or when made, they were not to a consistent point in space (not shown).

For some experiments, we examined the effects of varying stimulation amplitude to determine the threshold necessary to elicit saccadic responses. Electrical stimulation was applied in both voltage controlled and current controlled mode. The mean threshold for current mode was $40\pm12$ μA (n=6, mean±SD). The mean threshold for voltage mode was $2.5\pm0.6$ V (n=20). The mean prestimulation electrode impedance was $540\pm170$ kΩ at 1 kHz (n=56). Current mode stimulation had larger mean saccade endpoint cluster size ($1.2\pm0.6°$, n=14) than voltage mode stimulation ($0.7\pm0.4°$, n=42).

Figure 13:
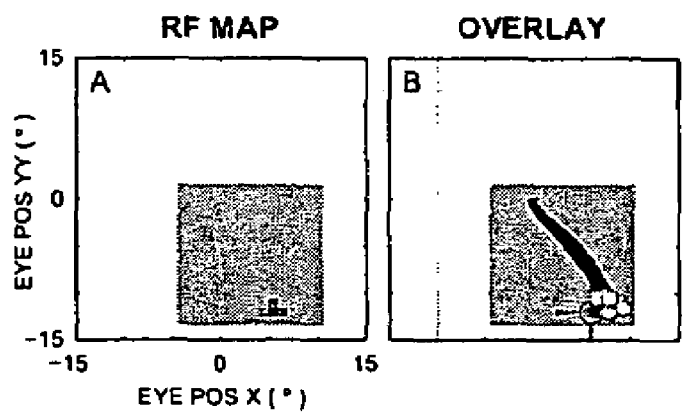
FIG. 13 is a schematic illustration depicting a comparison of receptive field center and electrical target saccade endpoints.
Figure 13:
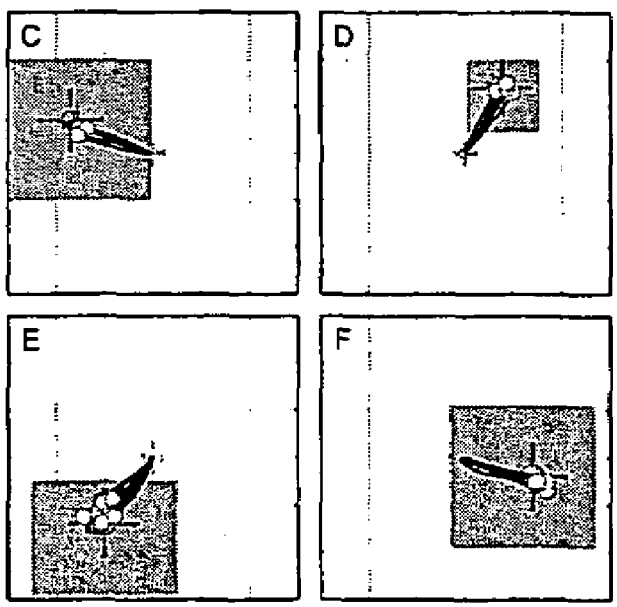
Figure 13:
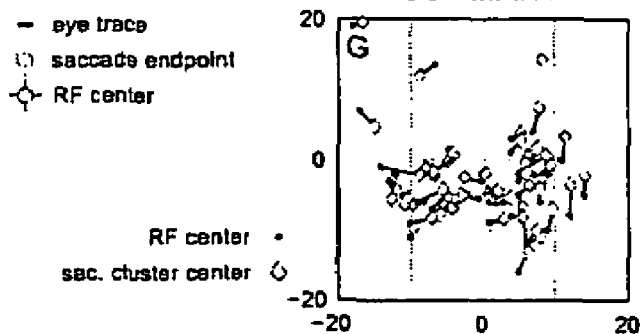
Figure 14:
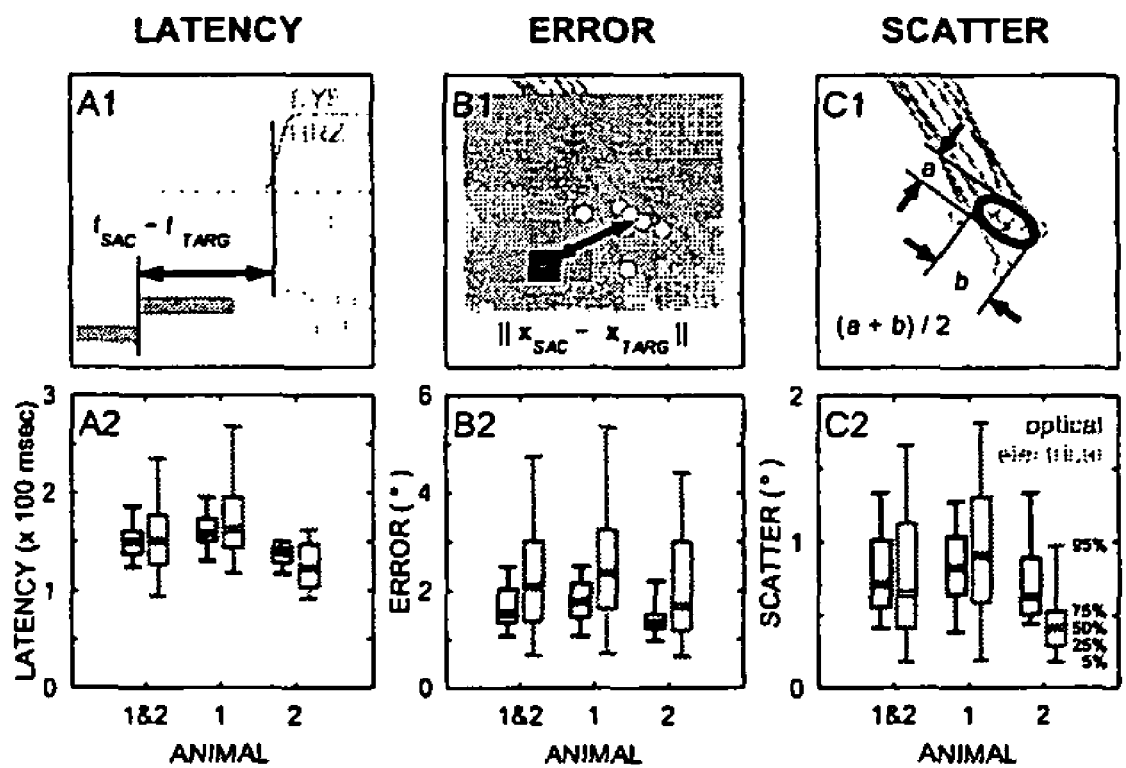
FIG. 14 is a schematic illustration depicting latency, accuracy, and repeatability associated with the experiments discussed in Example 2. The upper three panels depict three measures used to analyze saccade performance: latency, error, and scatter. The lower three panels give summary results from all three LGNs for optical and electrical saccades. Summary results are presented for the 56 experiments as box plots for optical (left) and electrical (right) conditions depicting the 5, 25, 50, 75, and 95th percentile levels in the lower bar, lower box edge, heavy bar, upper box edge, and upper bar, respectively. (A1) Latency was calculated as the difference in time between fixation offset (coincident with target onset) and saccadic response. The horizontal axis is time in a given trial. The two upper traces are the horizontal (HRZ) and vertical (VRT) components of eye position. The two lower traces are the final portion of the fixation point (FIX PT, enabled; FIX PT line, extinguished), and the period where the target was present (TARG box and line) for either optical or electrical targets. (A2) Optical and electrical saccades had identical average latencies for pooled data, although the distribution of electrical saccades was wider (124/137/150/160/186 ms at the 5/25/50/75/95 percentiles for optical and 94/126/150/177/235 ms for electrical). No significant differences were found between optical and electrical latencies for either animal. (B1) Error was calculated as the distance between target position or RF center and mean saccade endpoint. (B2) Optical error was slightly but significantly smaller than electrical error for pooled data (1.1/1.3/1.5/2.0/2.5° optical, 0.7/1.4/2.1/3.0/4.7° electrical, p<0.0005). Individual animal data had similar results (see main text). (C1) Scatter was calculated as the mean of the sizes of a two-dimensional Gaussian fitted to the saccade endpoint positions (1×sigma contour shown). (C2) Optical and electrical scatter were very similar (0.4/0.5/0.7/1.0/1.3° optical, 0.2/0.4/0.6/1.1/1.7° electrical) without statistical significance for pooled data and for Animal 1, although for Animal 2, electrical scatter was significantly less than optical scatter (p<0.002).

To compare endpoints in electrical trials against the visual responses for the electrode site, we overlaid the visual response (or receptive field, RF) map (FIG. 13A) with the saccades elicited for electrical targets (FIG. 13B). There was a strong correspondence between measured RF center and saccade endpoint, with saccade endpoints often covering the RF center. Sometimes a small offset was found between receptive field center and saccade endpoints, but this was also found for optical targets, as is typical for tasks where saccadic targets are extinguished before eye movements commence. Similar results were found for locations spanning all four quadrants of the visual field at eccentricities of 2-26° (FIG. 13). The saccade reaction times were comparable between optical and electrical stimulation (Animal 1: $160\pm18$ ms vs. $172\pm45$ ms, mean±SD, n=34, p>0.1 two tailed t-test; Animal 2: $137\pm10$ ms vs. $127\pm27$ ms, n=22, p>0.1; FIGS. 14A1 and 14A2). Since signals were being introduced into the LGN directly, we might have expected slightly faster reaction times to electrical targets than to optical targets, but that was not consistently seen. Because the task did not require that the animals react as quickly as possible, the fairly large spread in reaction times might have obscured slight differences between them. The speed-versus-distance relationship for saccades, known as the main sequence, was indistinguishable between electrical and optical targets (data not shown).

We examined the accuracy and repeatability of saccades to assess if electrically evoked percepts were at the receptive field location of nearby LGN neurons, as expected. For accuracy we examined the average distance between saccade endpoints and the appropriate target: the screen location for optical stimuli, the receptive-field location for electrical stimuli. For repeatability, we examined the size of endpoint clusters. The distance between the average saccade endpoint and appropriate target was somewhat greater for electrical ($2.3\pm1.2°$, mean±SD) than for optical ($1.7\pm0.5°$ saccades, but the means were not significantly different for two of the three LGNs (two-tailed t-test, p>0.3 with n=10, and p>0.05 with n=22 for Animal 1/L, and Animal 2/R, but p<0.005 with n=24 for Animal 1/R; FIGS. 14B1 and 1B2). The additional error in the electrical condition was not large and may be due in part to the 1° resolution used when measuring RF position. Monte-Carlo simulations suggest that quantization noise in RF position estimates would increase the mean observed error for electrical targets by about 0.1° over a noiseless measurement of RF position, explaining part but not all of the difference.

Repeatability, the size of endpoint clusters, was indistinguishable between optical saccades and electrical saccades ($0.8\pm0.3°$ vs. $0.8\pm0.5°$; FIGS. 14C1 and 14C2) for pooled data, although Animal 2 had significantly smaller scatter for electrical saccades ($0.8\pm0.3°$ vs. $0.5\pm0.3$, two-tailed t-test p<0.002). To within the limits of our behavioral assay, the animals could thus localize electrically evoked percepts at least as accurately as the 0.5° optical targets. Electrical stimulation was performed in both parvocellular and magnocellular subdivisions of the LGN. Electrode tracks were inferred from a three-dimensional model of the LGN using a combination of electrode depth, alternation of eye input, and the receptive-field location at each recording site along a penetration. 30 sites were tentatively identified as parvocellular and 26 as magnocellular based on these criteria. No statistically significant differences were found between parvocellular and magnocellular sites in the analysis presented above.

Figure 15:
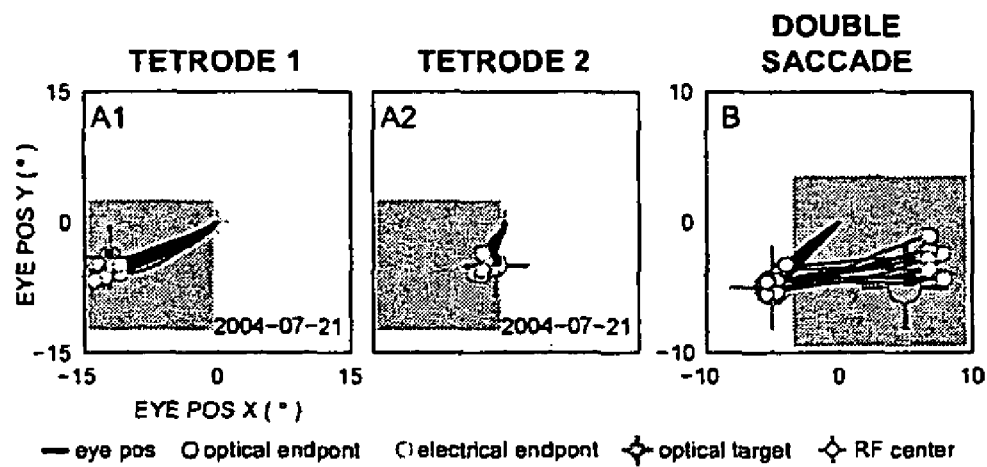
FIG. 15 is a schematic illustration showing discrimination between two electrodes (A1, A2), and a two target task (B). (A1, A2) Single experiment performed with two simultaneously implanted electrodes separated physically by approximately 1 mm along an oblique penetration in the LGN. The receptive field centers were separated in visual space by 10°. A slightly modified version of the primary experiment was performed where each electrode was randomly selected for stimulation in interleaved fashion. The animal was able to discern which electrode was stimulated 100% of the time. (B) A different experiment where two stimuli were presented in sequence, first an optical stimulus to the lower left of fixation, second an electrical stimulus with a previously measured RF center to the lower right. Eye position traces start at the central fixation point (not shown), saccade to the lower left with accurate landing at the optical target position (left crosshair), followed by a saccade to the right with accurate landing at the RF position (right crosshair) relative to the fixation point rather than to the optical target location or some intermediate point. This set of correct two-saccade sequences demonstrates that electrical stimulation is not directly evoking a saccade, but instead is creating a normal visual percept. The apparent overshoot and upward shift to the second target is typical of this task and was seen during training with two optical targets.

A small number of experiments (two in each animal) were performed with two tetrodes to simultaneously access different receptive field locations. Two electrodes were placed 10-15° apart in visual space and both animals were able to distinguish between interleaved stimulation to the electrodes with 100% accuracy (FIGS. 15A1 and 15A2). The spatial separation threshold for discrimination between two points was not tested.

The results presented above did not rule out the possibility that electrical stimulation in our task directly drives saccades, for instance by engaging motor pathways via retinal collaterals to the superior colliculus, or by retrograde stimulation of tectothalamic projections from the superior colliculus, rather than generating a visual percept to which the animal reacts. We therefore performed additional experiments (two in each animal) in which two targets were presented in quick succession and animals were required to saccade to them sequentially. Both targets in this protocol were extinguished before the animals began to respond. The temporal separation of the targets varied from experiment to experiment in the range of 30-80 ms. During training, both targets were optical; during subsequent data collection, the first target was optical and the second electrical. Both animals were able to perform the dual saccade task correctly. If the electrical and optical targets interfered, or if the phosphene was not perceived in spatial coordinates, the second saccade might be expected to land at a location relative to the first target, or a point in between the fixation point and the first target.

Instead the second saccade was to the RF center as originally measured relative to the fixation point (FIG. 15B), suggesting the electrical target created a phosphene that was interpreted in spatial coordinates unaffected by the intervening optical saccade.

The foregoing results were obtained with the following methods and materials.

Subjects

Two adult macaque monkeys (*Macaca mulatta*), one female and one male, were used in these experiments. The animals were chair trained and familiarized with the laboratory and handler before experiments commenced. A structural MRI was taken to guide the implantation of a cylindrical titanium recording chamber over a chronically maintained craniotomy with a vertical approach to the identified location of LGN. Additionally, a titanium headpost was affixed to the skull with titanium bone screws, and a scleral search coil implanted in one eye with leads routed to an external connector at either the headpost or the recording chamber. Surgical manipulations were performed using sterile techniques.

Electrodes

Tetrodes were constructed out of 13 and 15 micron polyimide coated tungsten wire (California Fine Wire, Grover Beach, Calif.) using a custom built twister. Tetrodes were advanced through the craniotomy and into the brain using a tapered trans-dural guide tube that was 32 ga (220 µm OD) for the distal 10 mm. For experiments with two tetrodes, both electrodes were advanced through the same guide tube but were differentially trimmed so that the ends were staggered by 1.5-2.0 mm. Electrode position in the horizontal plane was controlled with an X-Y stage (FHC Inc., Bowdoinham, Ma.), and depth was controlled with a hydraulic microdrive (David Kopf Instruments, Tujunga, Calif.).

Eye Position

Field coil driver and receiver circuitry was custom built. Eye positions were calibrated and corrected to within 2 percent full-scale error spanning the central 25° of the computer monitor. Calibrations were found to be stable within a recording session, with only minor adjustments necessary from day to day.

Apparatus

Training and recording sessions took place in a shielded, darkened room. Animals were seated in primate chairs (Crist Instrument Company, Hagerstown, Md.), and placed 30 cm away from a computer monitor (Model P225f, ViewSonic Corporation, Walnut, Calif.) running at 800 by 600 pixels with 180 Hz vertical refresh. Individual pixels on the screen spanned approximately 0.1° of visual space. Stimulus isolators (Model 2200, A-M Systems Inc., Sequim, Wash.) were driven in either voltage mode or current mode from a data sequencing and acquisition system (Power 1401, Cambridge Electronic Design, Cambridge, England). Stimulation was 5 to 200 ms long trains of 1 ms sinusoidal pulses repeating at 100 or 200 Hz. Stimulation was applied between neighboring leads of a single tetrode to ensure electric fields and currents would be highly focused and to strictly limit the volume of activated tissue. Because stimulation was applied between neighboring wires in a bundle rather than a single electrode and a remote return, the initial polarity of the stimulus (cathodic or anodic) was not uniquely defined. Behavioral control and stimulus presentation was performed using a custom software application. Off-line analysis was performed in Matlab (The Mathworks, Natick, Mass.).

Recording Location

A full-field alternating flicker stimulus was used to detect LGN as electrodes were advanced ventrally through the craniotomy. Electrodes were determined to be in LGN when all of the following criteria were met: responses to the search task were robust and clearly lateralized with at least one contralateral to ipsilateral transition (or the reverse) during penetration, perisaccadic bursts of activity were observed with every eye movement, and a focal receptive field map could be obtained with peak location consistent with other penetrations. In one animal, MRI-visible depositions were used to verify the location of the LGN.

Track Reconstruction

Using the laminar identification based on a full-field alternating flicker stimulus and RF positions measured for each recording location in a single penetration, probable electrode tracks were computationally reconstructed by selecting volumes of tissue with matching characteristics in a model LGN. Combining this with the electrode X-Y position within the recording chamber and the inter-location distance along a penetration produced a likely penetration path and therefore laminar identification for each recording site.

RF Mapping

Receptive-field maps were measured through a fixation task separate from the primary experimental task. Once the animal had fixated, a white-noise stimulus consisting of a 15-by-15 checkerboard of 100% contrast, black or white squares was shown over the RF location while neural activity was monitored. Sequence snippets 1-5 seconds long were used for each trial with 300-500 ms fixation before and after each snippet. Multi-unit activity was reverse correlated against the stimulus, pixel location by pixel location, to develop a response map according to standard techniques (Beckstead et al. 1983, Exp. Brain Res. 52:261-268). Sequences were pseudo-random with repeat period larger than the total presentation used in an entire block of mapping trials.

Monte-Carlo Simulation of RF Quantization Noise

Because RF centers were computed with 1° resolution, somewhat large as compared to the expected RF sizes for LGN at the 2-26° eccentricities studied, we performed a simulation to estimate the extent to which this uncertainty affected our electrical target error measurements. Data for optical targets, where the target location is set with 0.1° resolution, were used for this simulation. Optical target locations were perturbed in simulation with ±0.5° uniformly distributed noise in both x and y directions, equivalent to the quantization error for RF center measurements, and the incremental errors were determined for saccades to those targets as compared to the errors to unperturbed targets. A total of 100 simulations were performed with the entire set of optical targets, and the mean additional error was computed.

Other Embodiments

As discussed, active elements, both electrical and biological, that are used to generate phosphenes can be placed with either uniform or non-uniform density in order to approximate the natural non-uniform variation in resolution or to compensate for it and create a uniform resolution, respectively.

Figure 16:
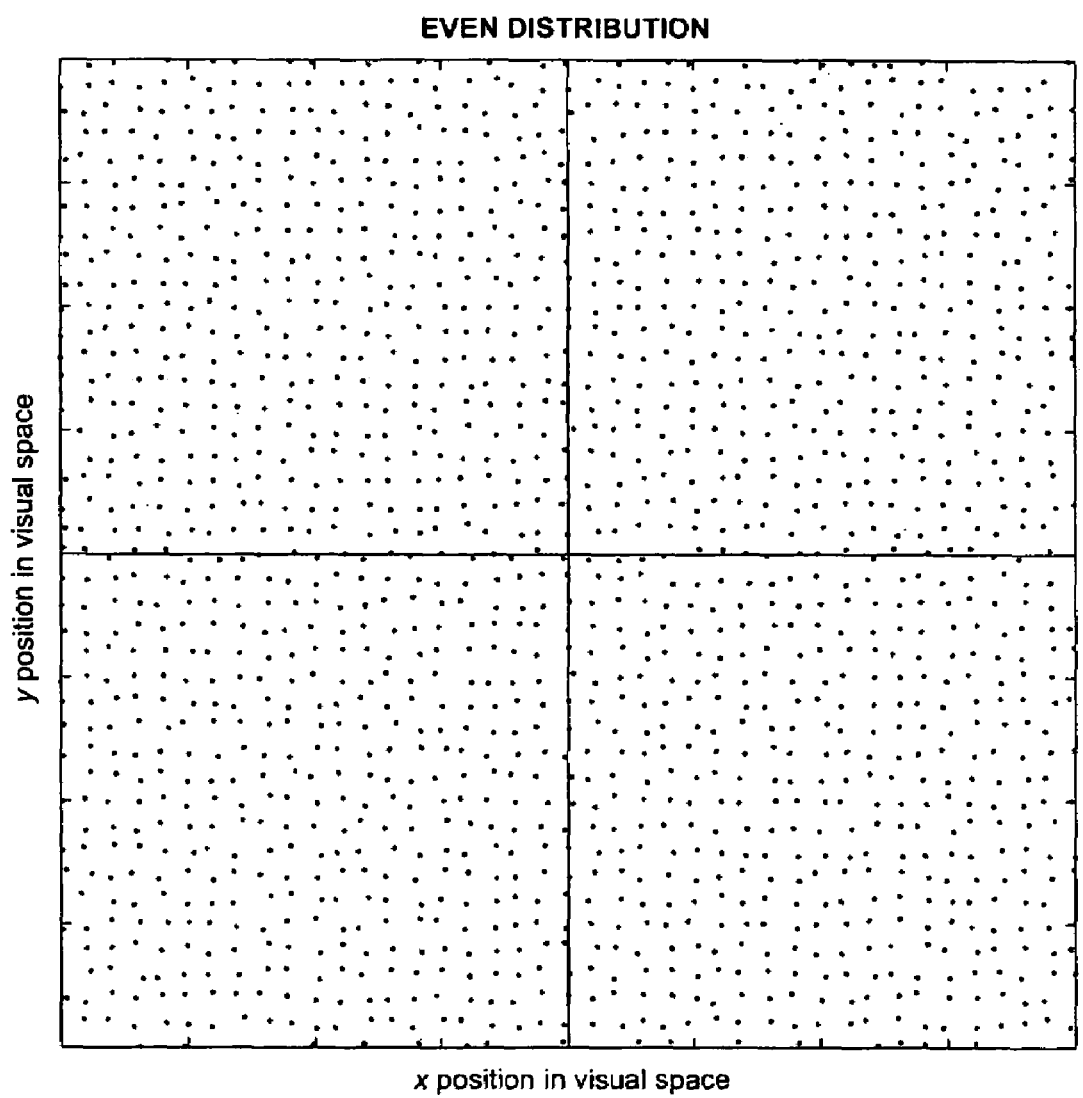
FIG. 16 is a schematic illustration showing an average uniform distribution of contact placement in two or tree dimensions across a target brain area.

Accordingly, in another aspect, the invention features a prosthesis device with an average uniform density of contact placement in two or three dimensions across a target brain area so as to achieve a non-uniform density of visual percepts, weighted toward the center of vision, approximating the natural non-uniform distribution of visual resolution (FIG. 16).

Figure 17:
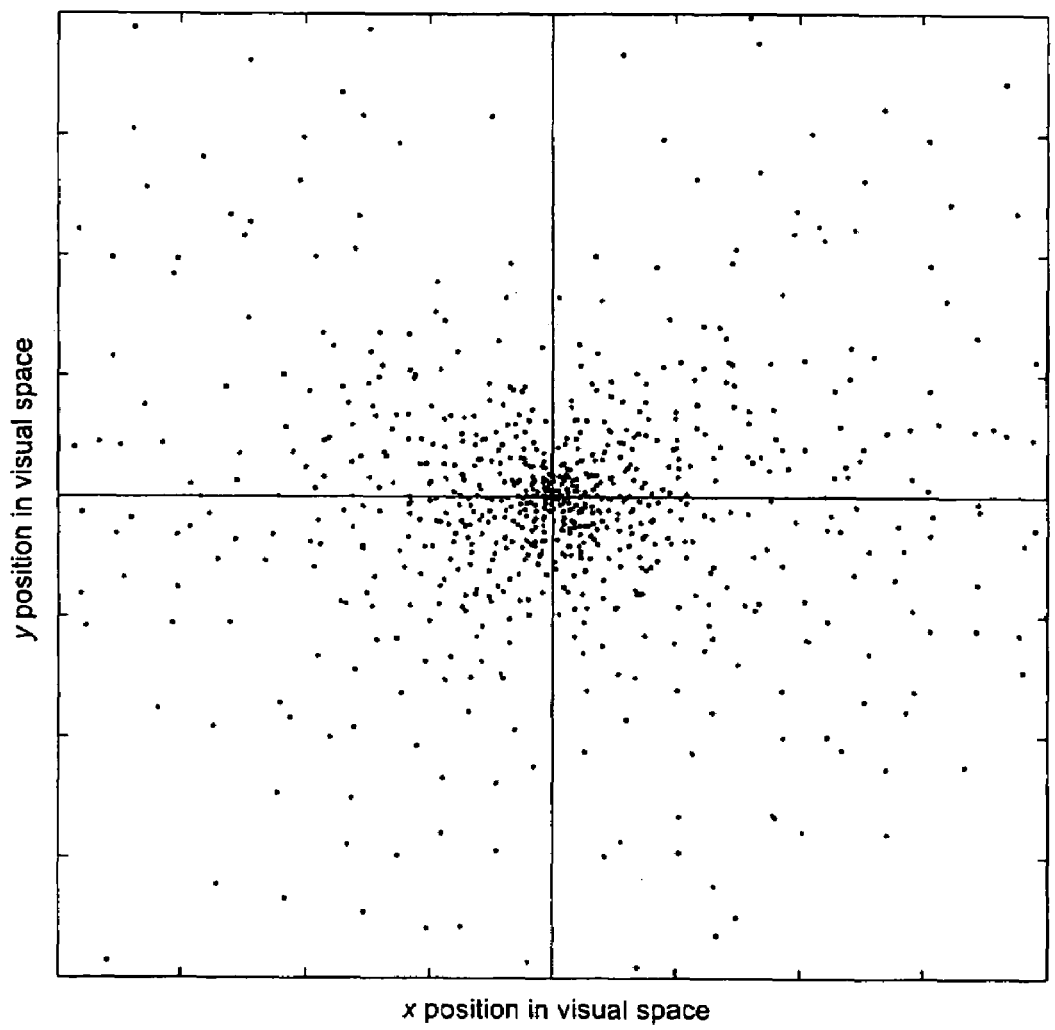
FIG. 17 is a schematic illustration showing a gaze point weighted distribution of contact placement in two or tree dimensions across a target brain area.

In a related aspect, the invention features a prosthesis device with a non-uniform density of contact placement in two or three dimensions across a target brain area so as to achieve a uniform density of visual percepts, approximating a non-natural even distribution of visual resolution (FIG. 17).

While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims.

Although the invention has been defined using the appended claims, these claims are illustrative in that aspects of the invention are intended to include the elements and steps described herein in any combination or sub combination. Accordingly, there are any number of alternative combinations for defining the invention, which incorporate one or more elements from the specification, including the description, claims, and drawings, in various combinations or sub combinations. It will be apparent to those skilled in the relevant technology, in light of the present specification, that alternate combinations of aspects of the invention, either alone or in combination with one or more elements or steps defined herein, may be utilized as modifications or alterations of the invention or as parts of the invention. It may be intended that the written description of the invention contained herein covers all such modifications and alterations.

We claim:

1. A method of providing a mammal with visual information from an artificial source, comprising;
    operatively connecting one or more electrodes to a lateral geniculate nucleus of the mammal;
    providing visual information from said artifical source;
    translating the visual information into an electrical signal;
    transmitting the electrical signal to the electrodes; and
    stimulating the lateral geniculate nucleus with the electrical signal through the electrodes in a manner to stimulate brain activity to recognize visual information.

2. The method of claim 1, further comprising creating a map of the electrode connected to the lateral geniculate nucleus.

3. The method of claim 1, wherein the visual information is hyperacute.

4. The method of claim 1, further comprising reading the position of an eye of the mammal to provide gaze information, wherein the gaze information determines the origin of visual information.

5. The method of claim 1, further comprising transmitting electrical power to the electrodes.

6. The method of claim 1, wherein the electrodes are of differing length.

7. The method of claim 1, wherein the electrodes are made of glial cells, cultured neurons, nerve bundles, copper, tungsten, titanium, platinum/iridium, insulated metallic wires, carbon, boron, silicon, or conductive fibers.

8. The method of claim 7, wherein the electrodes are coated with a biocompatible insulating surface comprising Teflon, parlene, formvar, silicone, native oxide, or a combination thereof.

9. The method of claim 1, wherein the electrodes are biological.

10. The method of claim 1, wherein the electrodes comprise electrically controlled neurons synapsing onto the lateral geniculate nucleus.

11. The method of claim 1, wherein the electrodes have a source of electrical power.

12. The method of claim 1, wherein the electrical signal comprises repetitive pulse waveforms.

13. The method of claim 12, wherein the repetitive waveforms are square waves, sinusoidal pulses, triangle waves, or square pulses.

14. The method of claim 1, wherein the electrical signal comprises patterned waveforms.

15. The method of claim 1, further comprising penetrating each layer of the lateral geniculate nucleus with at least one electrode.

16. The method of claim 1, further comprising penetrating each lateral geniculate nucleus with at least one electrode.

17. The method of claim 1, further comprising penetrating each layer of each lateral geniculate nucleus with at least one electrode.

18. The method of claim 1, wherein the electrical signals are transmitted wirelessly to the electrodes.

19. The method of claim 1, wherein the electrical signals are transmitted via biological leads to the electrodes.

20. The method of claim 1, wherein the electrical signals are transmitted via wire leads to the electrodes.

* * * * *

UNITED STATES PATENT AND TRADEMARK OFFICE
CERTIFICATE OF CORRECTION

PATENT NO. : 8,396,561 B2
APPLICATION NO. : 12/520741
DATED : March 12, 2013
INVENTOR(S) : John S. Pezaris et al.

Page 1 of 1

It is certified that error appears in the above-identified patent and that said Letters Patent is hereby corrected as shown below:

In the Specifications:

Column 1, line 12 under STATEMENT AS TO FEDERALLY SPONSORED RESEARCH, replace

"The invention was made with support from NIH under grant Nos. R01EY12815 and P30 EY12196. The government has certain rights to the invention."

with

--This invention was made with Government support under Grant No(s). EY012185, EY012196, and NS041851 awarded by the National Institutes of Health. The government has certain rights to this invention.--.

Signed and Sealed this
Twenty-third Day of July, 2013

Teresa Stanek Rea
*Acting Director of the United States Patent and Trademark Office*